United States Patent
Blazer-Yost

(10) Patent No.: US 9,579,335 B2
(45) Date of Patent: Feb. 28, 2017

(54) TREATMENT OF CYSTIC DISEASES

(71) Applicant: Indiana University Research and Technology Corporation, Indianapolis, IN (US)

(72) Inventor: Bonnie Blazer-Yost, Indianapolis, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 0 days.

(21) Appl. No.: 14/853,216

(22) Filed: Sep. 14, 2015

(65) Prior Publication Data

US 2016/0000814 A1 Jan. 7, 2016

Related U.S. Application Data

(63) Continuation of application No. 13/276,898, filed on Oct. 19, 2011, now abandoned.

(60) Provisional application No. 61/394,603, filed on Oct. 19, 2010.

(51) Int. Cl.
| | | |
|---|---|---|
| A01N 57/00 | (2006.01) | |
| A61K 31/675 | (2006.01) | |
| A61K 31/7024 | (2006.01) | |
| A61K 45/06 | (2006.01) | |

(52) U.S. Cl.
CPC ........ *A61K 31/7024* (2013.01); *A61K 31/675* (2013.01); *A61K 45/06* (2013.01)

(58) Field of Classification Search
USPC .......................................................... 514/89
See application file for complete search history.

(56) References Cited

U.S. PATENT DOCUMENTS

| | | |
|---|---|---|
| 6,294,580 B1 | 9/2001 | Willson et al. |
| 2008/0113996 A1 | 5/2008 | Brown |
| 2009/0197835 A1 | 8/2009 | Carter et al. |

FOREIGN PATENT DOCUMENTS

| | | |
|---|---|---|
| EP | 0032128 | 7/1981 |
| EP | 0008203 | 8/1982 |
| EP | 0155845 | 3/1985 |
| EP | 0139421 | 4/1988 |
| EP | 0177353 | 4/1990 |
| EP | 0208420 | 9/1991 |
| EP | 0257781 | 9/1991 |
| EP | 0319189 | 6/1992 |
| EP | 0489663 | 6/1992 |
| EP | 0332332 | 3/1993 |
| EP | 0332331 | 2/1994 |
| EP | 0428312 | 12/1994 |
| EP | 0528734 | 10/1996 |
| EP | 0508740 | 1/1997 |
| EP | 306228 | 11/1999 |
| WO | 9218501 | 10/1992 |
| WO | 9302079 | 2/1993 |
| WO | 9322445 | 11/1993 |
| WO | 9405659 | 3/1994 |
| WO | 0008002 | 2/2000 |
| WO | 0230895 | 4/2002 |
| WO | 02059098 | 8/2002 |
| WO | 02062774 | 8/2002 |
| WO | 03074495 | 9/2003 |

OTHER PUBLICATIONS

Belibi et. al. (Expert Opinion on Investigational Drugs (2010) 19:315-328).*
Tamaruya et al., Angew. Chem. Int. Ed., 43: 2834-37 (2004).

* cited by examiner

*Primary Examiner* — Marcos Sznaidman
(74) *Attorney, Agent, or Firm* — Stinson Leonard Street LLP

(57) ABSTRACT

The invention described herein pertains to the treatment of cystic diseases. More particularly, the invention described herein relates to methods for treating cystic disease using one or more lysophosphatidic acid antagonists, TMEM16a inhibitors, and/or peroxisome proliferator-activated receptor modulators.

11 Claims, 11 Drawing Sheets

TREATMENT OF CYSTIC DISEASES

CROSS-REFERENCE TO RELATED APPLICATIONS

This application is a continuation application of U.S. patent application Ser. No. 13/276,898 filed on Oct. 19, 2011, which claims the benefit under 35 U.S.C. §119(e) of U.S. provisional application Ser. No. 61/394,603, filed Oct. 19, 2010, the disclosures of which are incorporated herein by reference in their entireties.

TECHNICAL FIELD

The invention described herein pertains to the treatment of cystic diseases. More particularly, the invention described herein relates to methods for treating cystic disease using one or more lysophosphatidic acid antagonists, TMEM16a inhibitors, and/or peroxisome proliferator-activated receptor modulators.

BACKGROUND AND SUMMARY OF THE INVENTION

Polycystic kidney disease (PKD) is one of a group of ciliopathies characterized by the growth of fluid filled cysts in several organs, predominately in kidney tubules and liver bile ducts. This group of genetic diseases, that also includes Bardt Biedl syndrome, Meckel Gruber syndrome, nephronophthisis, and oral-facial-digital syndrome, have been linked by the findings that the mutated genes encode proteins located in the primary cilium of the epithelial cells that line the normal tubule or duct and ultimately line the cysts that form in these tissues. The genes encode proteins of a transient receptor potential $Ca^{2+}$ channel. While the proteins linked to the various ciliopathies are found in other subcellular structures including the tight junctions, the finding of commonality in the primary cilium combined with the postulated function of this structure as an osmotic or flow censor, has lead to the postulate that aberrant ciliary function underlies cyst formation and growth.

Growth of cysts may occur in various cystic diseases such as polycystic kidney disease (PKD), polycystic liver disease (PLD), Bardt Biedl syndrome, nephronophthisis, Meckel Gruber syndrome and oral-facial-digital syndrome. Additionally, aberrant cyst growth may occur that is not associated with these diseases. Without being bound by theory, it is believed herein that cyst expansion may be a function of the stimulation of ion secretory events that cause increased movement of electrolytes and, secondarily, water into the cyst lumen. It has been shown that in PKD renal tissue, those events may be caused by agents that increase intracellular cAMP which, in turn, stimulate ion channels in the apical plasma membrane (Ye & Grantham, N Engl J Med, 329: 310-313 (1993); Grantham et al., J Clin Invest 95:195-202 (1995); Mangoo-Karim et al., Am J Physiol 269:F381-388 (1995); Davidow et al., Kidney Int 50:208-218 (1996). These observations have been extended to liver cysts formed from the cholangiocytes which line the liver bile ducts (Muchatuta et al., Exper Biol Med 234:17-27 (2009). In agreement with this contention are studies done first in rodent models of PKD and currently in clinical trials, showing that for example antagonists of the vasopressin V2 receptor in renal cells inhibit cAMP formation and cyst growth (Gattone et al. Nat Med 9:1323-1336 (2003).

Autosomal dominant polycystic kidney disease (ADPKD) is characterized by the slow growth of multiple fluid-filled cysts in the kidney and liver. The factors involved in cyst growth or changes in the rate of cyst growth are unknown. However, previous studies have demonstrated that renal injury results in exacerbation of cyst growth. Cyst growth in autosomal dominant polycystic kidney disease (ADPKD) is a slow process that may proceed over decades. Despite the formation of multiple, large cysts during ageing, renal function is usually not severely compromised until the fifth decade of life but then declines rather precipitously. Renal injury or tubular cell damage exacerbates cyst formation and expansion.

Cyst growth is thought to result from stimulation of ion secretory events that cause increased movement of electrolytes and, secondarily, water into the cyst lumen resulting in cyst expansion. It has been observed that increased intracellular cAMP in PKD renal tissue stimulates ion channels, predominately the cystic fibrosis transmembrane conductance regulator (CFTR) in the apical membrane, and also in the cholangiocytes that line liver bile ducts. Similarly, in rodent models of PKD and currently in clinical trials, it has been shown that antagonists of the vasopressin V2 receptor in renal cells or somatostatin agonists in cholangiocytes and renal tissue inhibit both cAMP formation and cyst growth.

However, pharmaceutical agents in clinical trials are reported interfere with the action of hormones that increase cAMP in target cells. In the kidney, antidiuretic hormone (ADH; vasopressin) regulates salt and water balance via a signaling pathway that increases intracellular cAMP. In the bile ducts, somatostatin, via a separate hormone receptor, decreases intracellular cAMP. In addition to mediating hormone action, cAMP also causes an increase in activity of the CFTR (cystic fibrosis transmembrane regulator) channel that transports $Cl^-$ into the cysts with the consequent movement of fluid and cyst expansion.

Thus, agents that decrease cAMP, such as vasopressin receptor antagonists, such as in the kidney, or somatostatin receptor agonists, such as in hepatic bile ducts, have been the subject of investigation for decreasing cyst growth. However, those agents may have limited utility because they are organ specific. Further, those agents may be prone to the side effects because they will likely also interfere with natural hormone signaling. Thus, there is yet a need for pharmaceutical agents capable of targeting the organ systems that are affected by cystic diseases such as PKD, PLD, Bardt Biedl syndrome, nephronophthisis. Meckel Gruber syndrome and oral-facial-digital syndrome, as well as other cystic formations not associated with these diseases.

It has been discovered herein that treatment with LPA antagonists that block the ability of LPA to interact with its receptor may inhibit electrolyte and fluid secretion and thereby block cyst initiation and/or growth. Thus, these agents are useful in preventing cyst formation and/or expansion in the kidney and hepatic bile ducts as well as in any other organs that are normally lined with polarized epithelial cells and show cyst formation during disease progression, such as the pancreas. Therefore, LPA antagonists are useful in the treatment of and/or prevention of cysts.

Using the mpkCCD$_{cl4}$ cell line model of renal principal cells, it has been discovered herein that LPA (lysophosphatic acid), a component of cyst fluid, is a factor that stimulates secretory $Cl^-$ transport via at least two anion channels. The LPA effect is manifested via receptors located on the basolateral membrane of the polarized renal principal cells and stimulates channel activity in the apical membrane. The concentrations of LPA measured in human cyst fluid and serum are sufficient to maximally stimulate ion transport. Without out being bound by theory, it is believed herein that renal injury and subsequent blood or cyst fluid seepage into the interstitial space is capable of providing a secretory stimulus to remaining, intact cysts resulting on overall cyst growth.

Further, cyst fluid obtained from human patients can stimulate secretory activity when added to renal epithelial cells. It has been reported that lipid-like component(s) of the cyst fluid could stimulate this Cl$^-$ secretory activity in both Madin Darby Canine Kidney (MDCK) cells and in primary cultures of ADPKD cells, and it has been suggested that the major active component in the cyst fluid is an endogenous forskolin.

In order to fully characterize the Cl$^-$ secretory response, electrophysiological techniques have been used herein to examine the effect of cyst fluid when added to a murine cell culture model of the principal cells, the mpkCCD$_{cl4}$ (mouse principal cells of the kidney cortical collecting duct, clone 4). In this model, human renal cyst fluid stimulates at least two different Cl$^-$ channels.

It has been discovered herein that the active component of the cyst fluid used in these studies is lysophosphatic acid (LPA) present in the cyst fluid in a concentration that maximally stimulates ion transport. In addition, it has been discovered herein that LPA concentrations in normal serum are also capable of maximally stimulating the Cl$^-$ transporters. Under normal conditions, the LPA is bound to proteins in the cyst fluid or bloodstream and, therefore, unavailable for binding to the LPA receptors on the basolateral membrane of the epithelial cells lining the cysts. Under conditions such as injury or loss of cyst wall integrity due to aging and/or cyst size, the LPA-protein complexes would be released into the interstitial space where they interact with specific receptors to exacerbate cyst growth.

It has also been discovered herein that treatment with inhibitors of TMEM16a may inhibit electrolyte and fluid secretion and thereby block cyst initiation and/or growth. Thus, these agents are useful in preventing cyst formation and/or expansion in the kidney and hepatic bile ducts as well as in any other organs, such as the pancreas. Therefore, TMEM16a inhibitors are useful in the treatment and/or prevention of cysts.

It has also been discovered herein that treatment with peroxisome proliferator-activated receptor (PPAR) modulators, such as PPAR gamma modulators may inhibit electrolyte and fluid secretion and thereby block cyst initiation and/or growth. Thus, these agents are useful in preventing cyst formation and/or expansion in the kidney and hepatic bile ducts as well as in any other organs, such as the pancreas. Therefore. PPAR gamma modulators are useful in the treatment and/or prevention of cysts.

In one embodiment, described herein are methods for treating cystic diseases in a patient, where the methods include the step of administering a therapeutically effective amount of one or more LPA receptor antagonists. In another embodiment, described herein are methods for treating cystic diseases in a patient, where the methods include the step of administering a therapeutically effective amount of one or more TMEM16a inhibitors. In another embodiment, described herein are methods for treating cystic diseases in a patient, where the methods include the step of administering a therapeutically effective amount of one or more PPAR gamma modulators.

In another embodiment, described herein are methods for treating cystic diseases in a patient, where the methods include the step of administering a therapeutically effective amount of one or more LPA receptor antagonists and one or more TMEM16a inhibitors. In another embodiment, described herein are methods for treating cystic diseases in a patient, where the methods include the step of administering a therapeutically effective amount of one or more LPA receptor antagonists and one or more PPAR gamma modulators. In another embodiment, described herein are methods for treating cystic diseases in a patient, where the methods include the step of administering a therapeutically effective amount of one or more TMEM16a inhibitors and one or more PPAR gamma modulators. In another embodiment, described herein are methods for treating cystic diseases in a patient, where the methods include the step of administering a therapeutically effective amount of one or more LPA receptor antagonists, one or more TMEM16a inhibitors, and one or more PPAR gamma modulators.

In another embodiment, described herein are methods for reducing electrolyte and fluid secretion in a patient having or suspected of having a cystic disease. The methods include the step of administering to the patient (a) an effective amount of one or more TMEM16a inhibitors; and (b) an effective amount of one or more lysophosphatidic acid antagonists, or an effective amount of one or more PPAR gamma agonists, or a combination thereof.

In another embodiment, described herein are methods for reducing cyst growth in a patient having or suspected of having a cystic disease. The methods include the step of administering to the patient (a) an effective amount of one or more TMEM16a inhibitors; and (b) an effective amount of one or more lysophosphatidic acid antagonists, or an effective amount of one or more PPAR gamma agonists, or a combination thereof.

Simultaneously, an equal volume of media was added to apical side to equalize the volumes.

Figure 4:
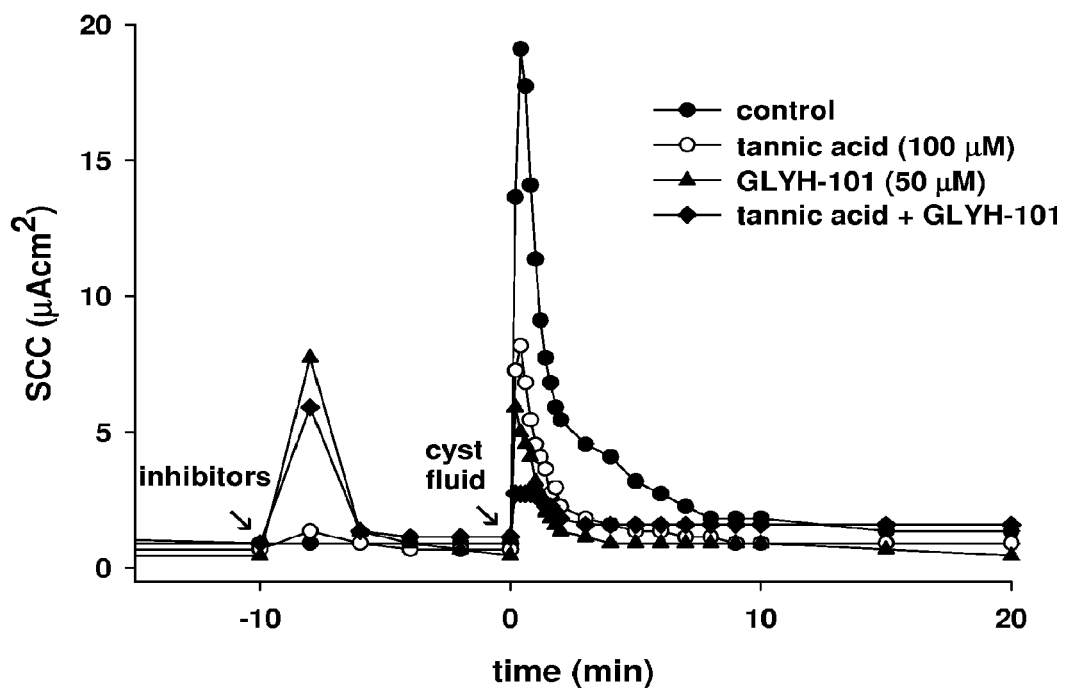

FIG. 4: Effect of chloride channel inhibitor pretreatment on cyst fluid stimulation of ion transport in the mpkCCD$_{cl4}$ cell line. Four cultures of mpkCCD$_{cl4}$ cells were grown in parallel on the same Transwell plate and analyzed in tandem. Inhibitors are added at time −10 minutes with the control receiving diluent only. At time t=0, identical aliquots (10% final volume) of the same cyst fluid were added to the serosal side of all four experimental tissues. Simultaneously, an equal volume of media was added to apical side to equalize the volumes.

Figure 5:
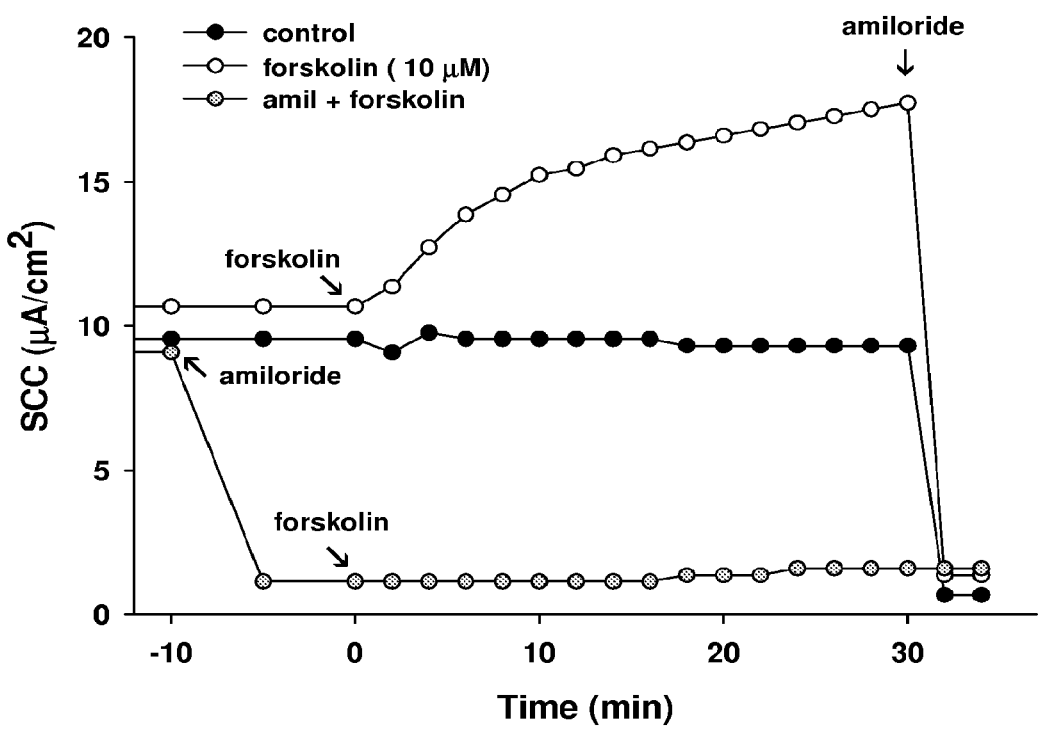

FIG. 5: Forskolin-stimulated ion transport in the mpkCCD$_{cl4}$ cell line. Three cultures of mpkCCD$_{cl4}$ cells were grown in parallel on the same Transwell plate and analyzed in tandem. After a stabilization period, amiloride ($10^{-5}$M) was added to the apical bathing media of one of the three cultures (t=−10 minutes). At time zero, forskolin was added to one of the cultures that was not pretreated and to the one that was pre-treated with amiloride. The remaining culture received diluents only and served as a control. 30 minutes after the addition of forskolin, amiloride ($10^{-5}$ M) was added to all cultures.

Figure 6:
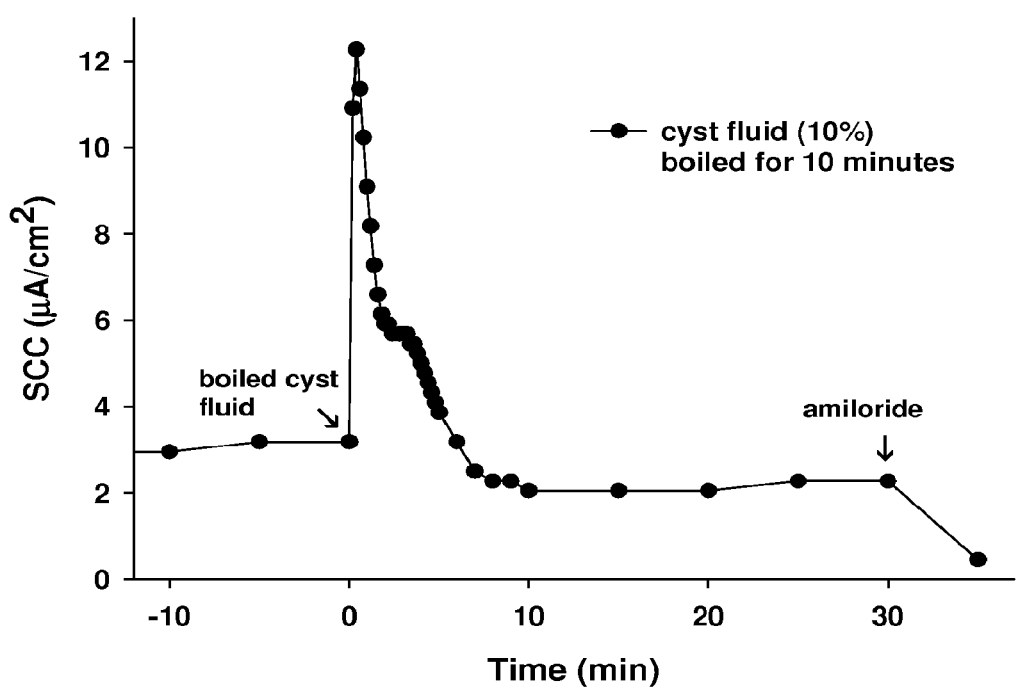

FIG. 6: Boiled cyst fluid stimulation of ion transport in the mpkCCD$_{cl4}$ cell line. mpkCCD$_{cl4}$ cells were grown to confluency on permeable Transwell supports and net ion transport was measured as short circuit current (SCC). At time t=0 minutes, cyst fluid that had been boiled for 10 minutes was added to the apical bathing media to obtain a final concentration of 10%. An equal volume of incubation medium was added to the contralateral side to balance the addition of the cyst fluid.

Figure 7:
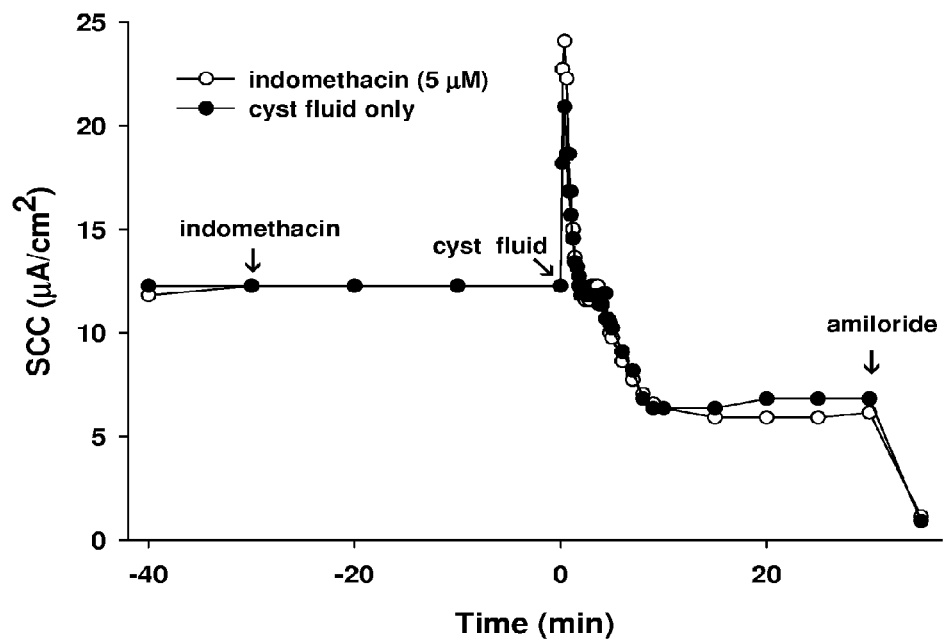
Figure 7:
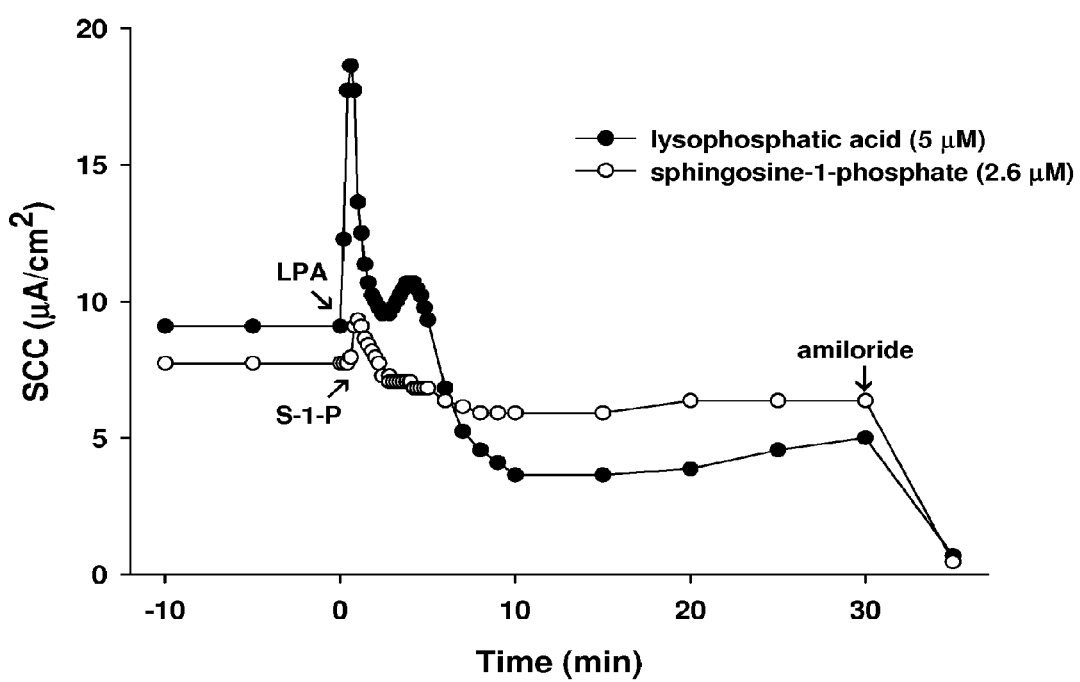
Figure 7:
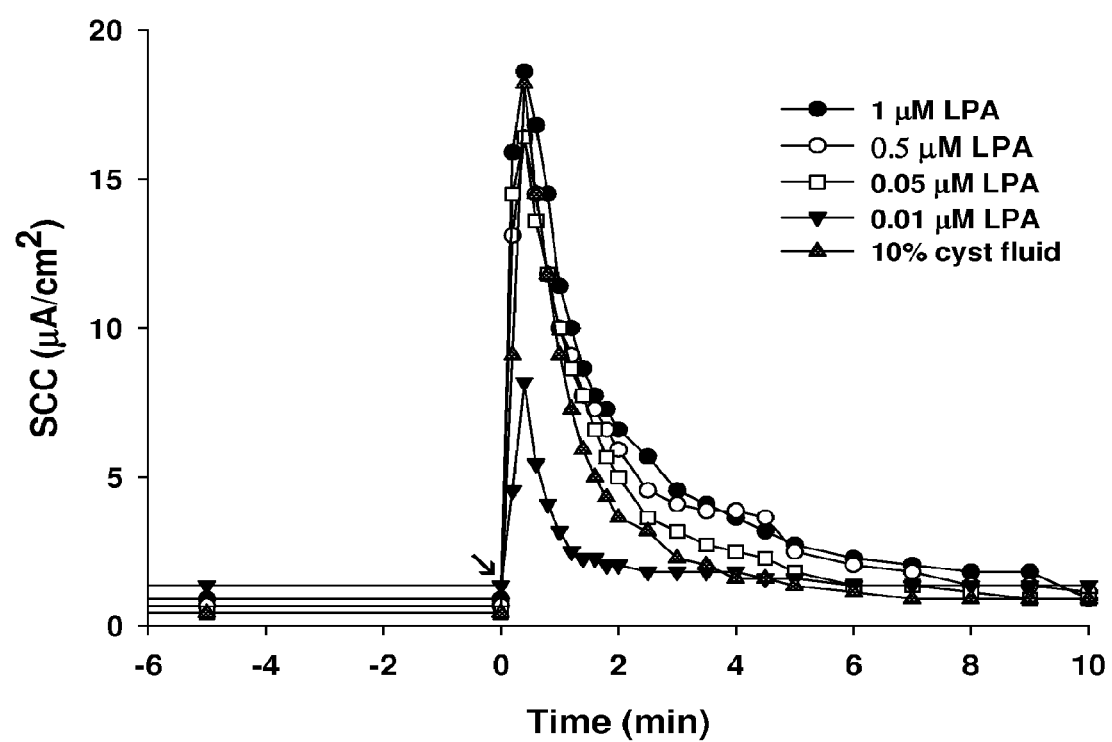

FIG. 7: Lipid effectors in cyst fluid stimulation of ion transport in the mpkCCD$_{cl4}$ cell line. mpkCCD$_{cl4}$ cells were grown to confluency on permeable Transwell supports and net ion transport was measured as short circuit current (SCC). A: Indomethacin was added to one of two cultures at time t=30 minutes. At time T=0 identical aliquots of cyst fluid were added to the controls and indomethacin-treated cultures. 30 minutes after the addition of the cyst fluid, amiloride ($10^{-5}$ M) was added to the apical bathing solution. B: Maximal concentrations of lysophosphatidic acid (LPA) or sphingosine-1-phosphate (S-1-P) were added to the basolateral bathing media at time t=0. 30 minutes after the addition of the lipid mediators, amiloride ($10^{-5}$ M) was added to the apical bathing solution. C: Limited dose response relationship for LPA stimulation of ion transport compared with the response to human renal cyst fluid. All cultures used for this series were grown and analyzed in parallel. At time t=0, LPA or cyst fluid (as indicated) were added to the basolateral bathing media.

Figure 8:
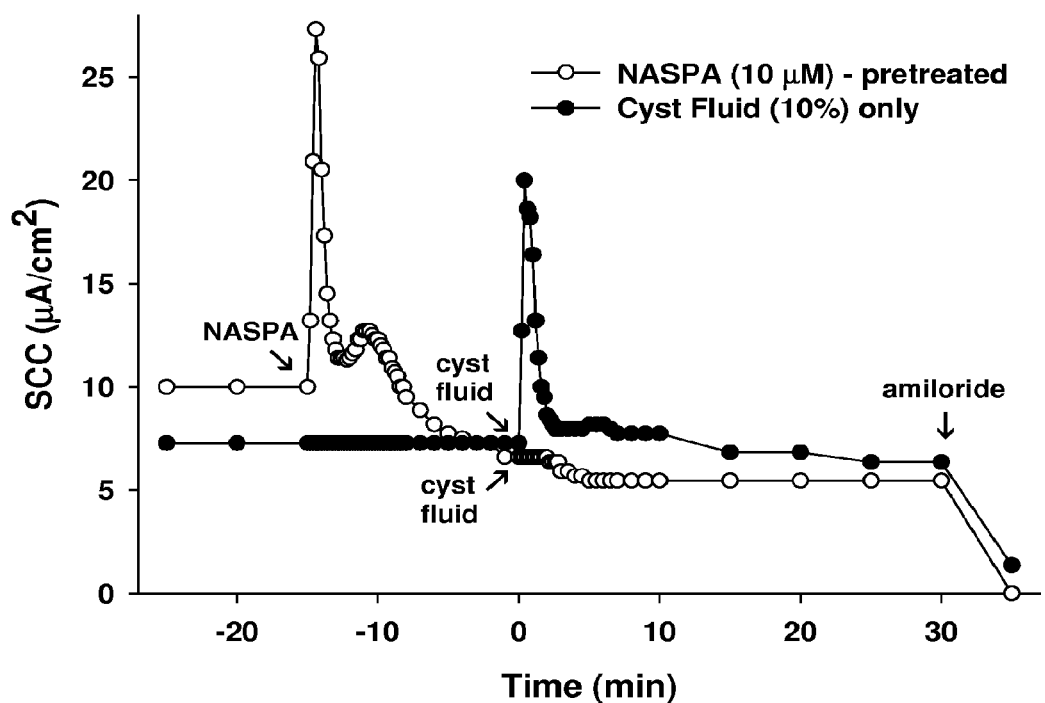
Figure 8:
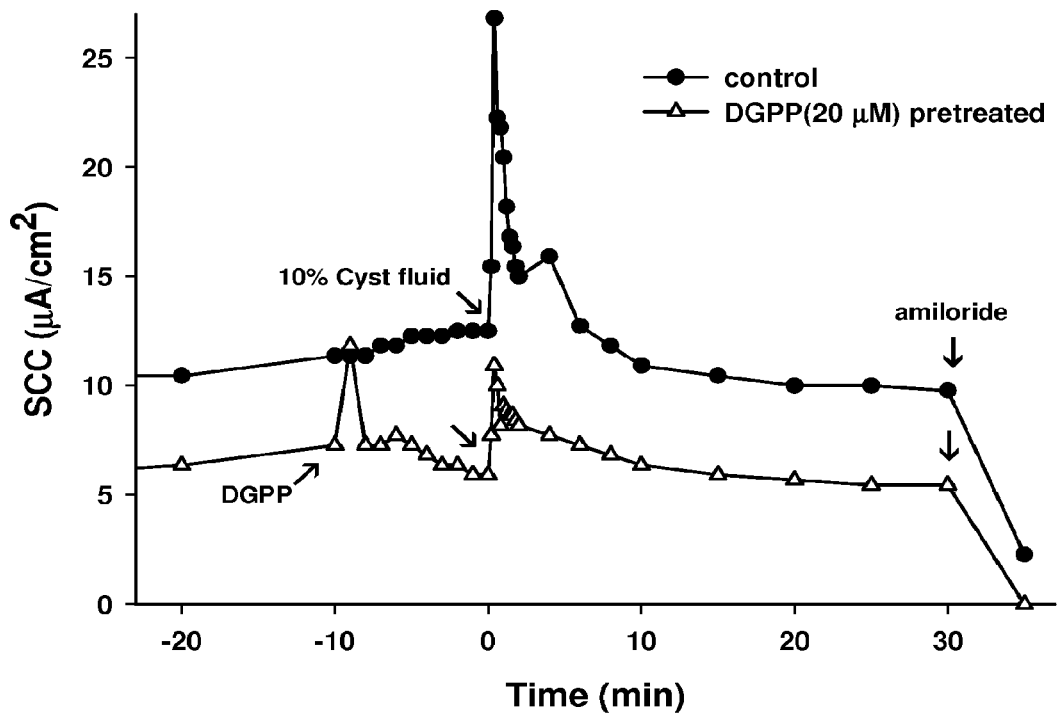
Figure 8:
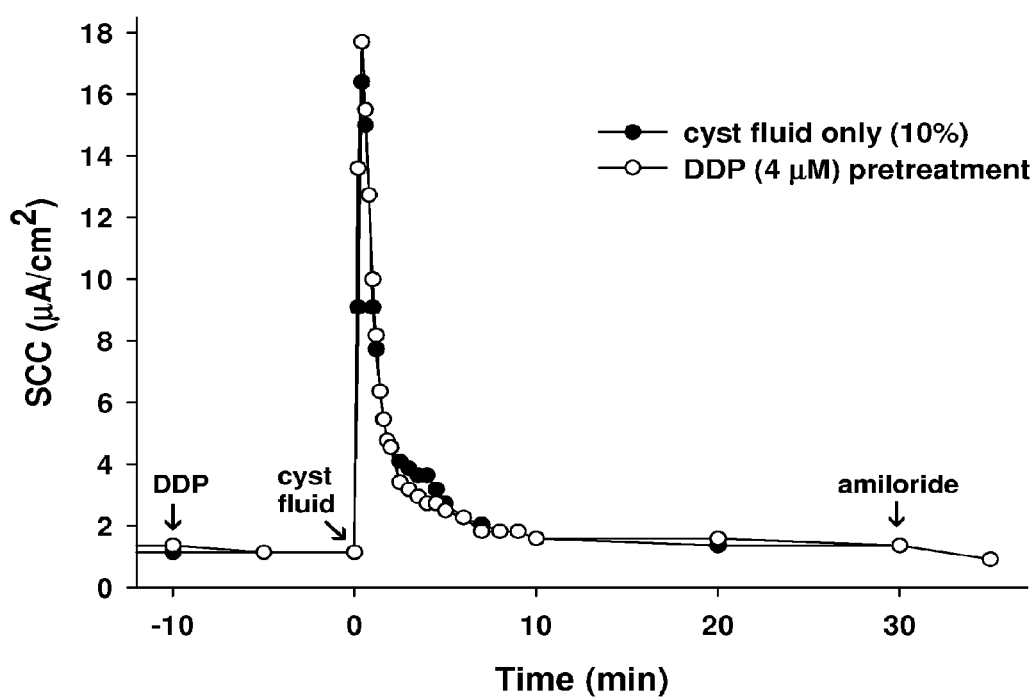

FIG. 8: Effect of LPA receptor agonists/antagonists on cyst fluid stimulation of ion transport in the mpkCCD$_{cl4}$ cell line. A: Effect of L-NASPA (N-palmitoyl-L-serine phosphoric acid) pretreatment on cyst fluid stimulated ion transport. 10 µM L-NASPA was added to one of two cultures of mpkCCD$_{cl4}$ cells grown in parallel at time t=−15 minutes. At time t=0 identical aliquots of cyst fluid were added to both the L-NASPA pre-treated and control monolayers. B. Effect of DGPP (diacylglycerol pyrophosphate) pretreatment on cyst fluid stimulated ion transport. 20 µM DGPP was added to one of two cultures of mpkCCD$_{cl4}$ cells grown in parallel at time t=−10 minutes. At time t=0 identical aliquots of cyst fluid were added to both the DGPP pre-treated and control monolayers. C. Effect of DDP (dodecylphosphate) pretreatment on cyst fluid stimulated ion transport. 4 µM DDP was added to one of two cultures of mpkCCD$_{cl4}$ cells grown in parallel at time t=−10 minutes. At time t=0 cyst fluid was added to both the DDP pre-treated and control monolayers. In all experiments, 30 minutes after the addition of the cyst fluid, amiloride ($10^{-5}$ M) was added to the apical bathing solution.

Figure 9:
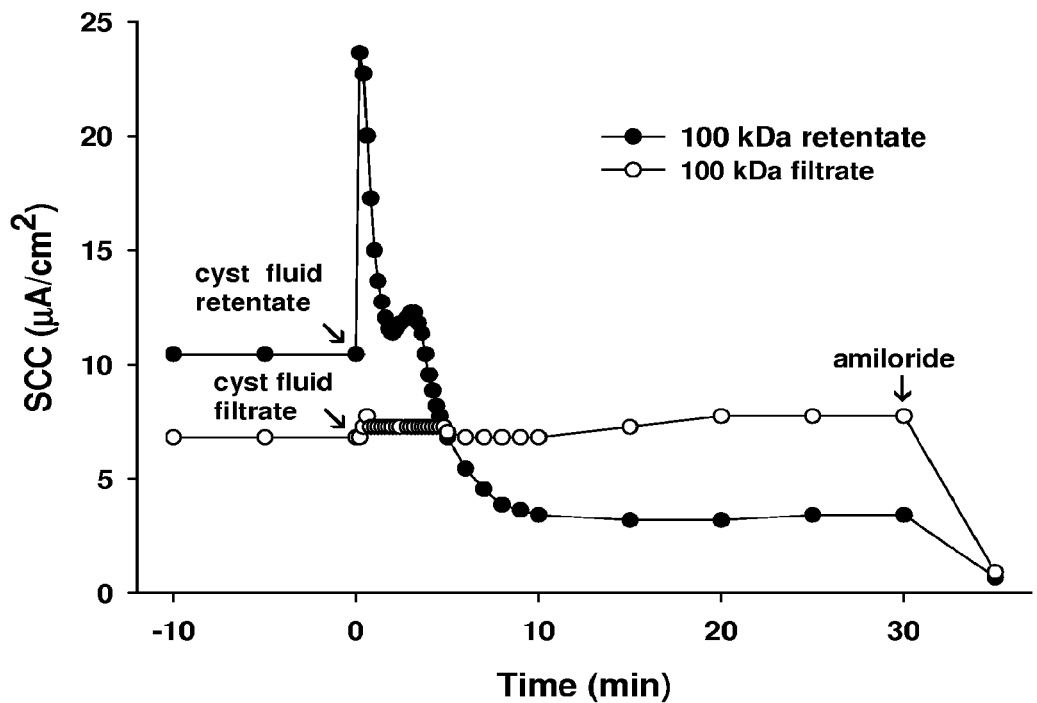

FIG. 9: Stimulation of ion transport using size fractionated cyst fluid. Cyst fluid was fractionated using Centriprep centrifuge filters with a 100 kDa cutoff. The fitrate was added to one of two mpkCCD$_{cl4}$ cultures to obtain a final concentration of a 10%. The retentate was returned to the original cyst volume and was subsequently added at a final concentration of 10%. 30 minutes after the addition of the cyst fluid fractions, amiloride ($10^{-5}$ M) was added to the apical bathing solution.

Figure 10:
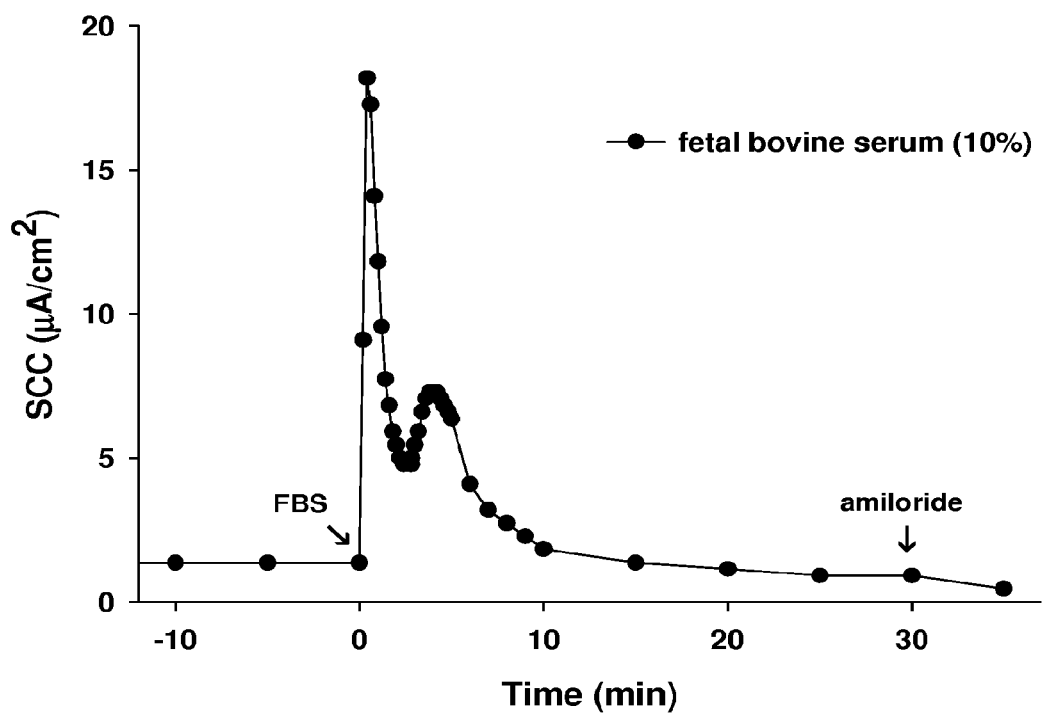

FIG. 10: Stimulation of ion transport using fetal bovine serum. At time t=0, FBS was added to the serosal bathing media to obtain a final concentration of 10%. An equal volume of media was simulataneously added to the basolateral bathing media. 30 minutes after the addition of FBS, amiloride ($10^{-5}$ M) was added to the apical bathing solution.

Figure 11:
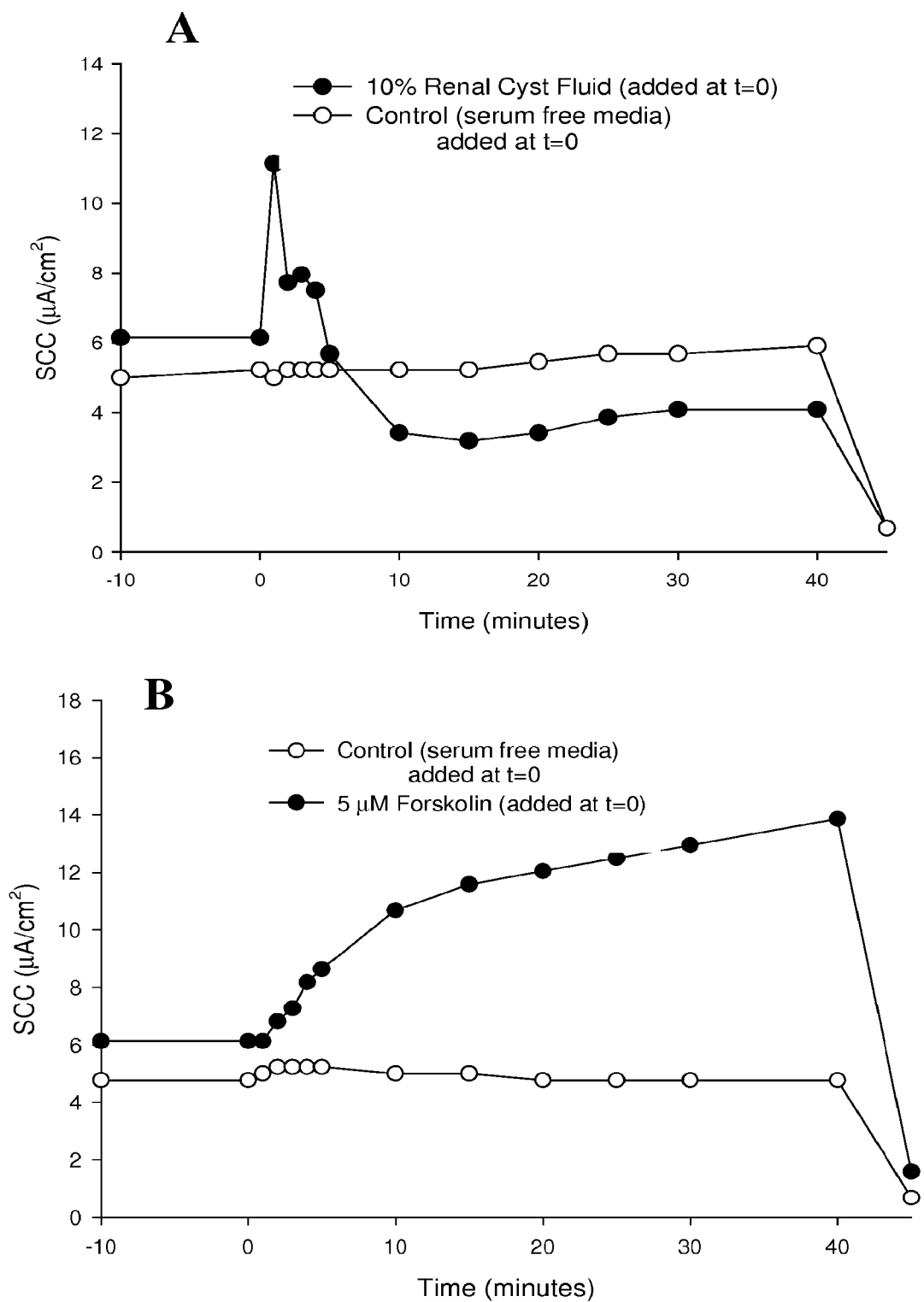

FIG. 11: Comparison of Ion Transport Stimulated in Response to Human Cyst Fluid With the Response to Forskolin. Electrophysiological responses of mpkCCDc17 cells to 10% human renal cyst fluid (panel A) and forskolin (panel B). Amiloride (10 µM final concentration) was added to each set-up at time=40 minutes. Panel A is representative of five separate experiments and panel B of four experiments.

Figure 12:
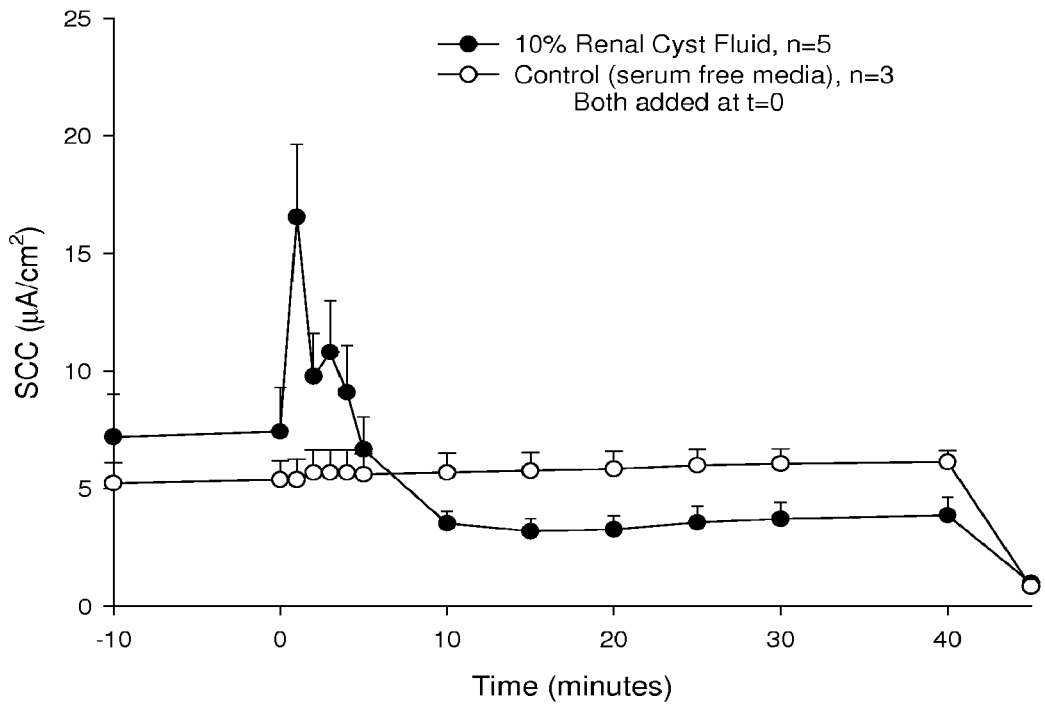
Figure 12:
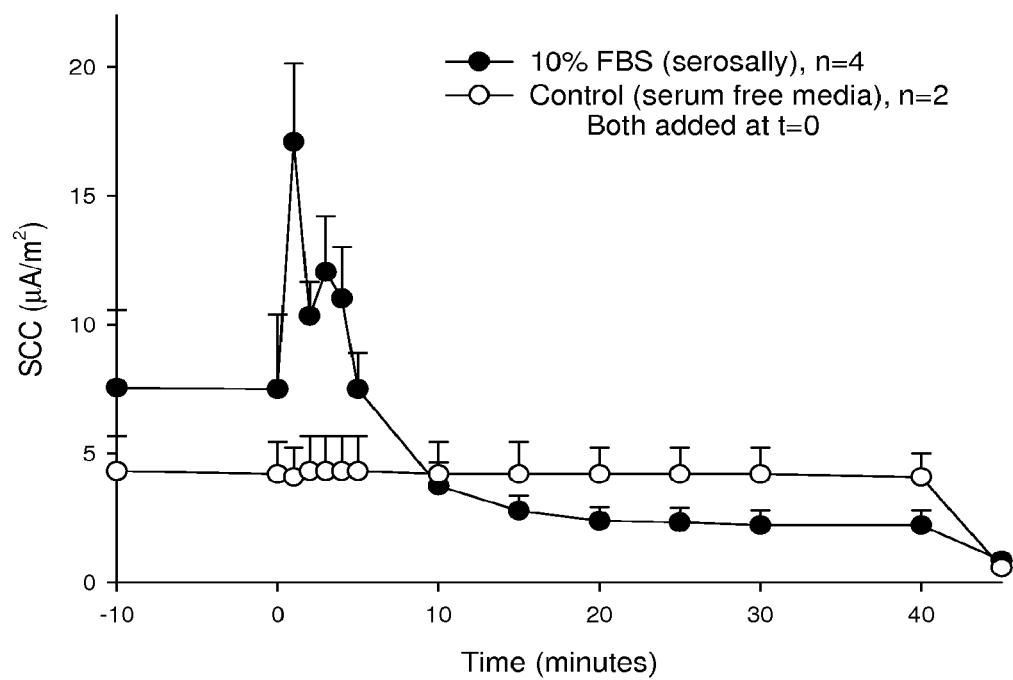
Figure 12:
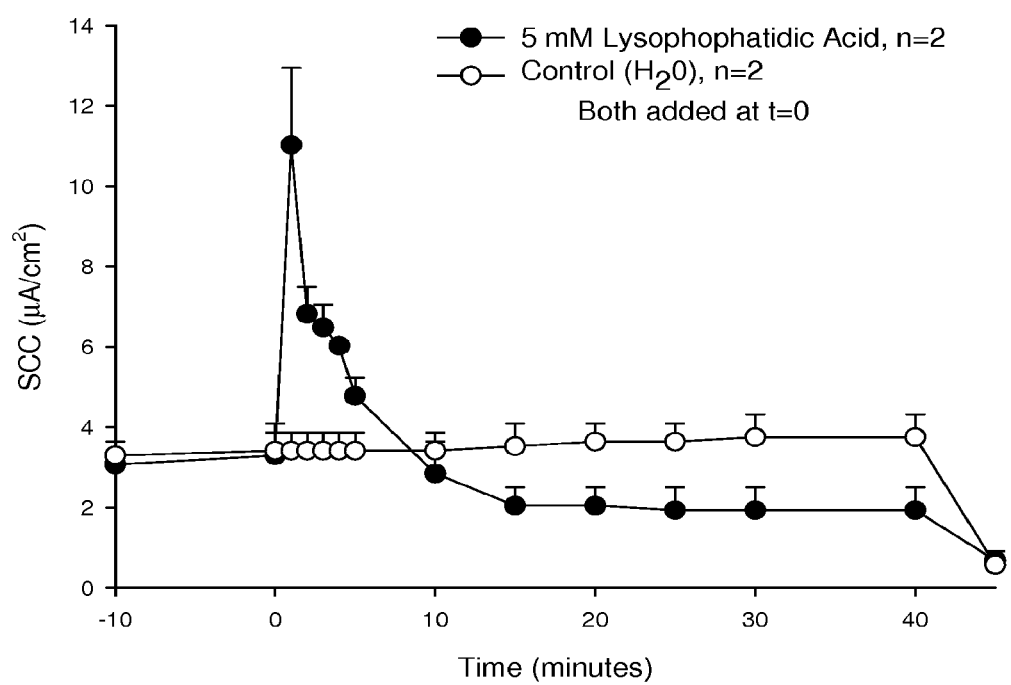

FIG. 12: Electrophysiological responses of mpkCCDc17 cells to cyst fluid, fetal bovine serum, and lysophosphatidic acid. Similarities of the electrophysiological responses of mpkCCDc17 cells to 10% human renal cyst fluid (panel A), 10% fetal bovine serum (panel B), and 5 µM lysophosphatidic acid (panel C). Amiloride (10 µM final concentration) was added to each set-up at time=40 minutes.

DETAILED DESCRIPTION

In one embodiment, methods for treating cystic diseases in a patient are described. The methods include administering to the patient a therapeutically effective amount of one or more lysophosphatidic acid receptor antagonists, and one or more TMEM16a inhibitors, and/or one or more PPAR gamma modulators.

In another embodiment, the lysophosphatidic antagonist is selected from the group consisting of DGPP, Carbohydrate compound 14, Ki16425, VPC 12204, VPC 12249, VPC 12249-10t, VPC 12249-10t-13d, VPC 32179, VPC 32183, VPC 12031, Thio-ccPA-18:1, Thio-ccPA-16:0, CHF-ccPA, Palmitoyl α-bromomethylene phosphonate, Palmitoyl α-chloromethylene phosphonate, Palmitoyl α-H2-methylene phosphonate, Palmitoyl α-OH-methylene phosphonate, Oleoyl sn-2-AO-LPA, Palmitoyl sn-2-AO-LPA, Alkoxymethylene-phosphonate-LPA (18:1), Alkoxymethylene-phosphonate-LPA (16:0). FAP-10. FAP-12, SPH, SPP, N-palmitoyl-1-serine, N-palmitoyl-1-tyrosine, 2-Amino-3-oxo-3-(tetradeeylamino)propyl dihydrogen phosphate, 2-(Acetylamino)-3-oxo-3-(tetradecylamino) propyl dihydrogen phosphate, 2-Amino-3-(octadecylamino)-3-oxopropyl dihydrogen phosphate, 1,2-(3-Octadecyloxypropane)-bis(dihydrogen phosphate), 1,2-(3-Docosanoyloxypropane)-bis(dihydrogen phosphate), Phosphoric acid monobutyl ester. Phosphoric acid monooctyl ester, Phosphoric acid monooctadecyl ester, Phosphoric acid monodocosyl ester. Acyl LPG 18:1, DPIEL, LPG 14:0, 2(s)-OMPT, 3-(N-((2-(2-((pyridin-3-ylmethylamino)carbonyl)phenyl)phenyl)carbonyl)-N-(2-(2,5-dimethoxyphenyl-)ethyl)amino)propanoic acid hydrochloride, methyl 3-(14-[4-(1[1-(2-chlorophenyl) ethoxy]carbonyl}amino)-3-methyl-5-isoxazolyl] benzyl}sulfanyl) propanoate, and 4'-1[(3-phenylpropyl)(3,4, 5-trimethoxybenzoyl)amino]methyl}-2-biphenylyl)acetic acid, and VPC51299.

In another embodiment, the lysophosphatidic antagonist is selected from the group consisting of DGPP, Carbohydrate compound 14, Ki16425, VPC 12204, VPC 12249, VPC 12249-10t, VPC 12249-10t-13d, VPC 32179, VPC 32183, VPC 12031, Thio-ccPA-18:1, Thio-ccPA-16:0, CHF-ccPA, 2-Amino-3-oxo-3-(tetradeeylamino)propyl dihydrogen phosphate, 2-(Acetylamino)-3-oxo-3-(tetradecylamino) propyl dihydrogen phosphate, 2-Amino-3-(octadecylamino)-3-oxopropyl dihydrogen phosphate, 1,2-(3-Octadecyloxypropane)-bis(dihydrogen phosphate), 1,2-(3-Docosanoyloxypropane)-bis(dihydrogen phosphate), Phosphoric acid monobutyl ester, Phosphoric acid monooctyl ester, Phosphoric acid monooctadecyl ester, Phosphoric acid monodocosyl ester, Acyl LPG 18:1, DPIEL, LPG 14:0, 2(s)-OMPT, 3-(N-((2-(2-((pyridin-3-ylmethylamino) carbonyl) phenyl)phenyl)carbonyl)-N-(2-(2,5-dimethoxyphenyl-) ethyl)amino)propanoic acid hydrochloride, methyl 3-(14-[4-(1[1-(2-chlorophenyl)ethoxy]carbonyl}amino)-3-methyl-5-isoxazolyl]benzyl}sulfanyl)propanoate, and 4'-1[(3-phenylpropyl)(3,4,5-trimethoxybenzoyl)amino]methyl}-2-biphenylyl)acetic acid, and VPC51299.

In another embodiment, the lysophosphatidic antagonist is selected from the group consisting of DGPP, Carbohydrate compound 14, Ki16425, L-NASPA, VPC 12204, VPC 12249, VPC 12249-10t, VPC 12249-10t-13d, VPC 32179, VPC 32183, VPC 12031, Thio-ccPA-18:1, Thio-ccPA-16:0, CHF-ccPA, Palmitoyl α-bromomethylene phosphonate, Palmitoyl α-chloromethylene phosphonate, Palmitoyl α-H2-methylene phosphonate. Palmitoyl α-OH-methylene phosphonate, Oleoyl sn-2-AO-LPA, Palmitoyl sn-2-AO-LPA, Alkoxymethylene-phosphonate-LPA (18:1), Alkoxymethylene-phosphonate-LPA (16:0), FAP-10, FAP-12, SPH, SPP, N-palmitoyl-1-serine, N-palmitoyl-1-tyrosine, 2-Amino-3-oxo-3-(tetradeeylamino)propyl dihydrogen phosphate, 2-(Acetylamino)-3-oxo-3-(tetradecylamino) propyl dihydrogen phosphate, 2-Amino-3-(octadecylamino)-3-oxopropyl dihydrogen phosphate, 1,2-(3-Octadecyloxypropane)-bis(dihydrogen phosphate), 1,2-(3-Docosanoyloxypropane)-bis(dihydrogen phosphate), Phosphoric acid monobutyl ester. Phosphoric acid monooctyl ester, Phosphoric acid monooctadecyl ester, Phosphoric acid monodocosyl ester, Acyl LPG 18:1, DPIEL, LPG 14:0, 2(s)-OMPT, 3-(N-((2-(2-((pyridin-3-ylmethylamino)carbonyl)phenyl)phenyl)carbonyl)-N-(2-(2,5-dimethoxyphenyl-) ethyl)amino)propanoic acid hydrochloride, methyl 3-(14-[4-(1[1-(2-chlorophenyl)ethoxy]carbonyl}amino)-3-methyl-5-isoxazolyl]benzyl}sulfanyl) propanoate, and 4'-1[(3-phenylpropyl)(3,4,5-trimethoxybenzoyl)amino]methyl}-2-biphenylyl)acetic acid.

In another embodiment, the lysophosphatidic antagonist is VPC51299.

In another embodiment, the LPA antagonist is a cyclic sulfuric acid analog of 2-oleoyl LPA, such as described in Tamaruya et al., Angew. Chem. Int. Ed., 43: 2834-37 (2004), the disclosure of which is incorporated herein by reference.

Additional illustrative examples of lysophosphatidic antagonists are disclosed in U.S. Patent Application Publication Number 20090197835 by Carter et al., the disclosure of which is incorporated herein by reference in its entirety.

Additional illustrative examples of lysophosphatidic acid inhibitors include antibodies that bind to one or more LPA receptors. The antibody may possess specificity for $LPA_1$, $LPA_2$, $LPA_3$, $LPA_4$, $LPA_5$ receptors, or any combination thereof. Antibodies directed against LPA receptors may be generated using routine methods for antibody production according to procedures well known to those skilled in the art.

In another embodiment, the TMEM16a inhibitor is tannic acid, or a pharmaceutically acceptable salt, thereof, or a prodrug of any of the foregoing.

In another embodiment, the PPARγ modulators are agonists. Illustrative PPARγ agonists include thiazolidinediones (also referred to as glitazones).

In another embodiment, the PPAR gamma modulator is a thiazolidinedione, or a pharmaceutically acceptable salt thereof are described. In another embodiment, the PPAR gamma modulator is selected from the group consisting of rosiglitazone, pioglitazone, and analogs and derivatives thereof, and combinations of there foregoing are described.

In another embodiment, the PPAR gamma modulator is selected from the group consisting of rosiglitazone (specific formulations of which are also known as AVANDIA) and analogs and derivatives thereof, pioglitazone (specific formulations of which are also known as ACTOS) and analogs and derivatives thereof, troglitazone (specific formulations of which are also known as REZULIN) and analogs and derivatives thereof, farglitazar (GI2570) and analogs and derivatives thereof, MCC-555 and analogs and derivatives thereof, rivoglitazone and analogs and derivatives thereof, ciglitazone and analogs and derivatives thereof, and combinations thereof. Illustrative PPARα/γ modulators include muraglitazar and analogs and derivatives thereof, tesaglitazar and analogs and derivatives thereof, aleglitazar and analogs and derivatives thereof, and the like.

In another embodiment, the PPAR gamma modulator is as described in European Patent 306228. The foregoing publication, and each publication cited herein, is incorporated herein by reference. In another embodiment, the PPAR gamma modulator is 5-[4-[2-(N-methyl-N-(2-pyridyl) amino)ethoxy]benzyl]thiazolidine-2,4-dione (rosiglitazone), including salts thereof, such as the maleate salt described in WO94/05659. In another embodiment, the PPAR gamma modulator is described in European Patent Applications, Publication Numbers: 0008203, 0139421, 0032128, 0428312, 0489663, 0155845, 0257781, 0208420, 0177353, 0319189, 0332331, 0332332, 0528734, 0508740; International Patent Application, Publication Numbers 92/18501, 93/02079, 93/22445 and U.S. Pat. Nos. 5,104,888 and 5,478,852. In another embodiment, the PPAR gamma modulator is 5-[4-[2-(5-ethyl-2-pyridyl)ethoxy]benzyl]thiazolidine-2,4-dione (pioglitazone), 5-[4-[(1-methylcyclohexyl)methoxy]benzyl]thiazolidine-2,4-dione (ciglitazone), 5[[4-[(3,4-dihydro-6-hydroxy-2,5,7,8-tetramethyl-2H-1-benzopyran-2-yl)met-hydroxy]phenyl]methyl]-2,4-thiazolidinedione (troglitazone) and 5-[(2-enzyl-2,3-dihydrobenzopyran)-5-ylmethyl)thiazolidine-2,4-dione (englitazone).

In another embodiment, the PPAR gamma agonist is not a thiazolidinedione but instead 0- and N-substituted derivatives of tyrosine. Illustrative PPAR gamma agonists are described in U.S. Pat. No. 6,294,580. In another embodiment, the PPAR gamma agonist is N-(2-benzoylphenyl)-O-[2-(5-methyl-2-phenyl-4-oxazolyl)ethyl]-L-tyrosine, 2(S)-(2-benzoyl-phenylamino}-3-{4-[2-5-methyl-2-phenyl-oxazol-4-yl)-ethoxy]phenyl}-propionic acid, (farglitazar), or GI262570. Farglitazar may be prepared by conventional methods, or as described in US Patent Applications Publication No. 20080113996.

In another embodiment, the PPAR gamma agonist is described in WO 02/062774, WO 02/30895, WO 00/08002, WO 02/059098, WO 03/074495.

In another embodiment, the PPAR gamma agonist is farglitazar, farglitazar sodium salt, rosiglitazone, rosiglitazone maleate salt, 2-({4-[({4-({4-[4-(ethyloxy)phenyl]-1-piperazinyl}methyl)-2-[4-trifluoromethyl)phenyl]-1,3-thiazol-5-yl}methyl)thio]phenyl}oxy)-2-methyl-propanoic acid, ({2-ethyl-4-[({4-({4-[4-(methyloxy)phenyl]-1-piperazinyl}methy-1)-2-[4-(trifluoromethyl)phenyl]-1,3-thiazol-5-yl}methyl)thio]phenyl}oxy)a-cetic acid, 2-{4-[{2-[2-fluoro-4-(trifluoromethyl)phenyl]-4-methyl-1,3-thi-azol-5-yl}methyl)sulfanyl]-2-methylphenoxy}-2-methylpropanoic acid. In this embodiment, the compounds may be prepared by conventional methods, or alternatively as described in WO 02/059098 and WO 02/062774.

In another embodiment, the PPAR gamma modulator is rosiglitazone, pioglitazone, and/or analogs and derivatives thereof having the following formula

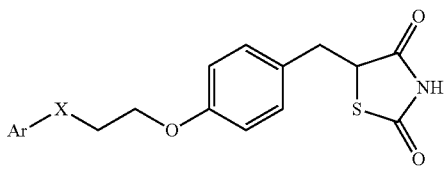

wherein Ar is an optionally substituted aryl or heteroaryl; and X is a bond, an optionally substituted alkylene, or $NR^1$, where $R^1$ is hydrogen or alkyl is described.

In another embodiment, the PPAR gamma modulator is ciglitazone, troglitazone, rivoglitazone, and/or analogs and derivatives thereof having the formula

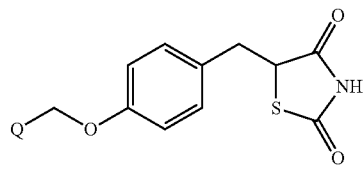

wherein Q is selected from the group consisting of cycloalkyl, benzocycloalkyl, heterocycloalkyl, benzoheterocycloalkyl, aryl, and heteroaryl, each of which is optionally substituted is described.

In another embodiment, the PPAR gamma modulator is englitazone, and/or analogs and derivatives thereof having the formula

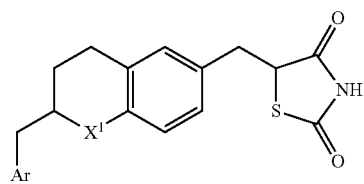

wherein $X^1$ is O, $NR^1$ or $CH_2$; and Ar is optionally substituted aryl or heteroaryl is described.

In another embodiment, the cystic disease is a liver, kidney, and/or pancreatic cystic disease.

In another embodiment, one or more lysophosphatidic acid antagonists are administered orally.

In another embodiment, one or more lysophosphatidic acid antagonists are administered via an implanted device or included in a matrix.

In another embodiment, one or more lysophosphatidic acid antagonists are administered by injection. Methods of injecting compounds, peptides, or antibodies in formulation may be accomplished using all known techniques, including but not limited to direct infusion, subcutaneous, parenteral, or intravenous injections. The injections may also be intrahepatic, intrarenal, and intrapancreatic. Direct infusions may be made into the target area via a catheter or other temporary or permanently implanted device. Illustratively, a substance may be infused directly into the blood vessels that supply the liver, kidney, or pancreas.

As used herein, the term "lysophosphatidic acid receptor antagonist" or LPA receptor antagonist generally refers to any substance that interferes with the binding and/or activity of lysophosphatidic acid at a physiological receptor. Illustratively, lysophosphatidic acid antagonists include compounds, antibodies, and the like, that bind to receptor targets of lysophosphatidic acid, including orthosteric or allosteric sites. As used herein, the term "therapeutically effective amount" generally means an amount of a lysophosphatidic acid antagonist that is capable of inhibiting cysts.

As used herein, the term "inhibiting" is understood to encompass preventing, blocking, stopping, or slowing the progression in any manner, including partially or completely reversing.

As used herein, the term "treatment of cystic disease" is understood to encompass inhibiting cyst formation or progression. It is also to be understood that the cysts may or may not be associated with polycystic kidney disease (PKD), polycystic liver disease (PLD), Bardt Biedl syndrome, nephronophthisis, Meckel Gruber syndrome, or oral-facial-digital syndrome.

As used herein, the term "patient" generally refers to any animal, including but not limited to humans and other mammals, such as dogs, cats, cows, horses, sheep, goats, pigs, and the like.

Without being bound by theory, it is believed that lysophosphatidic acid exerts physiological effects via binding to one or more of five lysophosphatidic acid receptors ($LPA_1$, $LPA_2$, $LPA_3$, $LPA_4$, and $LPA_5$). Lysophosphatidic acid antagonists are herein defined as molecules, including but not limited to organic compounds and peptides, which interfere with the binding of lysophosphatidic acid to a receptor. As used herein, a lysophosphatidic receptor is generally any protein molecule in a cell or on the surface of a cell to which lysophosphatidic acid can bind, causing a change in the activity of the cell. Such receptors may be coupled to G-proteins or ion channels.

Described herein is the method of short-circuit electrophysiology used for detailed examination of the nature of the ion channels stimulated in response to cyst fluid. These studies utilize mouse principal cells of the kidney cortical collecting duct, clone 4 ($mpkCCD_{cl4}$) cell line. These cells have the characteristics of the principal cell type found in the distal portion of the renal nephron. Principal cells often line renal cysts. It is found that human cyst fluid stimulated Cl⁻ secretion via the cystic fibrosis transmembrane transporter (CFTR). However, the activation of other ion channels by the fluid is also discovered. When examined in real time, the nature of channel activity by the cyst is observed to be quite different than the activity seen in response to forskolin (FIG. 11). These studies indicate that there are components found in cyst fluid that stimulate multiple ion transporters, which together cause electrolyte and fluid secretion into the cyst lumen.

The stimulatory activity from serum, cyst fluid, purified fractions of cyst fluid or exogenous LPA, is only seen when added to the serosal side of the cells. This phenomenon is analogous to adding the material to the outside of the cyst. Collectively, these data indicate that there are components from the serum that can stimulate secretory electrolyte and fluid movement. These components are not normally in direct contact with the basolateral membrane of the epithelial cells. Without being bound by theory, it is believed herein that in cystic diseases there is an increased vascular permeability that allows stimulatory serum components like LPA to directly interact with basolateral receptors on epithelial cells. These factors are not normally in direct contact with their cognate receptors on the basolateral membrane of the epithelial cells but are found in increased concentrations in the interstitial space due to a disease-related increase in vascular permeability. Without being bound by theory, it is believed that this activity causes an increase in transepithelial signaling, which stimulates ion transporters, and results in net electrolyte and fluid secretion.

Epithelial cells lining secretory or absorptive parts of organs have a polarized phenotype. When the epithelial monolayer is formed, the proteins and lipids of the apical membrane facing the luminal side are different than the proteins and lipids in the basolateral membrane facing the serosal side. The tight junctions maintain these differences.

Using electrophysiological techniques, it is shown herein that cyst fluid from ADPKD patients stimulates the activity of two distinct Cl$^-$ channels, CFTR and TMEM16a, in a murine cell line with characteristics of the principal cell type.

Human or bovine serum challenge mimics the response to cyst fluid. Human serum or plasma LPA levels will vary according to sample collection and storage conditions, gender and health of the individual. However, it is reasonable to assume that circulating levels in healthy individuals are in the low micromolar range. Applicant has found a maximal response to LPA concentrations at and above 0.05 µM indicating that serum contains sufficient LPA to maximally activate Cl$^-$ channels in renal cells. Likewise the cyst fluid contains sufficient LPA to maximally stimulate ion flux.

EXAMPLES

Example

Extensive analyses were conducted, including a proteomic determination of the cyst fluid. Cyst fluid was separated into fractions containing components with molecular weights greater and less than 100 kDa (CENTRICON-100, AMICON). The secretory activity remained in the retentate (substances>100 kDa) indicating the factor causing the secretion is larger than forskolin (MW 0.14 kDa). It was found that the stimulatory activity appears to be due to lysophosphatidic acid (LPA) bound to a group of large molecular weight binding proteins.

Proteomic analyses indicated most of these binding proteins were found predominately in the serum. Subsequent experiments indicated that serum, which contains 1-10 µM LPA, mimics the stimulatory activity of the cyst fluid when added directly to the normal renal cells (FIG. 12).

Example

Treatment of PCK rats with an LPA antagonist The PCK rat expresses many of the characteristics of human ADPKD but the mutation that causes the rodent form of the disease is orthologous to the human ARPKD gene, PKHD1, which encodes a protein called fibrocystin (Harric P C, Curr Opin Nephrol Hypertens 11:309-314 (2002)). These rodents develop both kidney and liver cysts and live long enough to facilitate testing of drugs post-weaning to 6-8 months of age. The PCK rat model has been used previously in tests for treatment options for PKD (Gattone et al., Nat Med 9:1323-1336 (2003); Putnam et al., J Am Soc Nephrol 18:934-43 (2007)).

PCK rats may be fed control or LPA antagonist-supplemented diets for 32 weeks starting 1 week after birth. Before weaning the animals may be fed using a liquid form of the diet delivered via pasteur pipette. After weaning the animals may be fed on the control or LPA antagonist-supplemented diet until week 32. PCK rats are bred to be homozygous for the mutation causing polycystic disease.

Animals may be routinely monitored during the entire 8 months. Alterations in the normal weight gain in the growing animals may be monitored. Lack of weight gain or weight loss would likely signify an adverse reaction to the test compound while an unusual weight gain in the test compound-treated group could indicate whole body edema. Animals may be weighed at least once a week and more often if indicated by the results.

Urines may be assessed weekly for proteinuria. Intermittent radiological imaging may be conducted to determine kidney and liver size in animals on both diets. Hematocrits and 24 hours urinary electrolytes may be measured periodically. Blood urea nitrogen (BUN) may be determined periodically to follow kidney function. At the end of the study the kidneys and livers can be used to assess and compare LPA antagonist effects on (1) overall animal health and survival; (2) kidney and liver weights as a function of overall body weight; (3) cystic volumes as a function of overall organ weight; (4) amount of fibrosis surrounding the renal and liver cysts; and (5) mitotic index of the epithelial cell layers surrounding the cysts.

Example

Treatment of BALB/c-cpk/cpk mice with an LPA antagonist. The BALB/c-cpk mouse is a non-orthologous model of ARPKD that exhibits both fast (heterozygous, cpk/cpk) and slow (homozygous, cpk/+) cystic development. In the BALB/c-cpk mouse model, the mutation causing the disease resides in a protein, cystin, and these animals have a different phenotype according to the gene dose. The homozygous animals rapidly develop polycystic kidney disease with the expression of multi-organ phenotype and die within 2-4 weeks. The heterozygous animals live to breeding age and after 12-18 months express large biliary cysts which are similar to those seen in children with ARPKD. In this model, the genetic cause of the disease is different from the PCK rat model and is, therefore, an alternative model of ARPDK. Further, these animals exhibit renal, hepatic, and pancreatic disease.

BALB/c-cpk/cpk homozygous mice may be fed control or LPA antagonist-supplemented diet starting at 5 days after birth. These animals may be sacrificed at day 17 because they normally die of renal failure by the third week. The compounds may be delivered in a liquid diet. Studies indicate that the animals will readily consume a compound fed to them via a pasteur pipette. BALB/c-cpk/+ heterozygous mice may be fed control or LPA antagonist-supplemented diet starting 5 days after birth and continued post weaning for 12 months.

The BALB/c-cpk/+ heterozygous animals have a relatively normal lifespan and begin to develop cysts, predominately hepatic bile duct cysts, at 6-8 months of age. Therefore, the heterozygous animals may be placed on antagonist-supplemented diets directly after weaning and may be monitored for 12 months.

In the BALB/c-cpk/cpk mice, BUN may be assayed on blood drawn at the time of sacrifice to determine renal function. The animals may be used to compare the effects of LPA antagonist on (1) kidney, liver, and pancreas weights as a function of overall body weight; (2) cystic volumes as a function of overall organ weight; and (3) amount of fibrosis surrounding the renal, liver, and pancreatic cysts.

In the BALB/c-cpk/+ heterozygous mice urines may be assessed weekly for proteinuria. Intermittent radiological imaging may be conducted to determine kidney, liver, and pancreas size. Hematocrits and 24 hours urinary electrolytes may be measured periodically during the study. Blood urea nitrogen may be assessed periodically to follow kidney function. These animals may be used to compare the effects of an LPA antagonist on: (1) overall animal health and survival; (2) kidney, liver, and pancreas weights as a function of overall body weight; (3) cystic volumes as a function of overall organ weight; (4) amount of fibrosis surrounding the renal, liver, and pancreatic cysts; and (5) mitotic index of the epithelial cell layers surrounding the cysts.

Example

Treatment of WPK rats with an LPA antagonist. The WPK rat is an orthologous, rapidly progressing, model of Meckel Gruber Syndrome. It is a rapidly progressing disease with both liver and kidney involvement. Thus, the use of an alternative, non-PKD model may facilitate a determination of whether LPA antagonists can inhibit several forms of ion-driven cystic disease.

WPK rats may be fed control or LPA antagonist-supplemented diets starting at 6 days after birth. These animals may be sacrificed at day 21 because they normally die of renal failure by the third week. The compounds may be delivered in a liquid diet. Studies indicate that the animals readily consume compounds fed to them via a pasteur pipette. Radiological determination as well as routine urine and blood chemistries may be conducted to document disease progression. At the end of each study, assessments made be made regarding (1) kidney and liver weights as a function of overall body weight; (2) cystic volumes as a function of overall organ weight; (3) amount of fibrosis surrounding the renal and liver cysts; and (4) mitotic index of the epithelial cell layers surrounding the cysts.

Each of rodent models described herein arise from separate mutations and express different time courses of disease progression. These models are useful for determining efficacy of drugs that can be used to treat cystic diseases that involve the activation of ion channels for cyst growth, including but not limited to ARPDK and ADPKD.

It is also possible to assess the efficacy of compounds that affect LPA binding and/or LPA mediated signaling in cases of very severe disease (BALB/c-cpk-cpk), and WPK where changes can be monitored during rapid progression to premature death from renal failure. The PCK and BALB/c-cpk/+ models additionally provide the ability to assess the effects of compounds that affect LPA on both kidney and liver cyst growth during slowly progressing disease.

Example

Treatment of Pkhd1 knockout mice with an LPA antagonist. Mutations in PKHD1 cause autosomal recessive polycystic kidney disease. The Pkhd1 knockout mouse is an animal model for cystic disease. In the Pkhd1lacZ/lacZ mouse, for example, exons 1-3 of the Pkhd1 gene are deleted and replaced with a lacZ reporter. These mice develop cysts in the pancreas and gall bladder, as well as the kidney.

Pkhd1 knockout mice may be fed with control or LPA antagonist-supplemented diets from day 5 after birth. The compounds may be delivered in a liquid diet. These animals can survive for several months, having cysts that begin to form within the first 2 months of life.

Therefore, the homozygous animals may be placed on antagonist-supplemented diets directly after weaning and may be monitored for 12 months.

In the Pkhd1 knockout mice, BUN may be assayed on blood drawn at the time of sacrifice to determine renal function. The animals may be used to compare the effects of LPA antagonist on (1) kidney, liver, and pancreas weights as a function of overall body weight; (2) cystic volumes as a function of overall organ weight; and (3) amount of fibrosis surrounding the renal, liver, and pancreatic cysts.

In the Pkhd1 knockout mice, urines may be assessed weekly for proteinuria. Intermittent radiological imaging may be conducted to determine kidney, liver, and pancreas size. Hematocrits and 24 hours urinary electrolytes may be measured periodically during the study. BUN may be assessed periodically to follow kidney function. These animals may be used to compare the effects of an LPA antagonist on: (1) overall animal health and survival; (2) kidney, liver, and pancreas weights as a function of overall body weight; (3) cystic volumes as a function of overall organ weight; (4) amount of fibrosis surrounding the renal, liver, and pancreatic cysts; and (5) mitotic index of the epithelial cell layers surrounding the cysts.

Example

Human renal cyst fluid collection. IRB approval for cyst fluid collection and tissue collection was secured prior to the initiation of this project. Cyst fluid was collected intraoperatively from patients undergoing either nephrectomies or cyst unroofing procedures. All human sample collections were obtained using deidentified containers in which only age and sex data was provided. All medical procedures were performed for reasons completely separate from the project reported in this manuscript. Once samples were delivered to the laboratory, the fluid was flash frozen in liquid nitrogen and stored at −80° C. until analyzed for biological activity.

Example mpkCCD$_{cl4}$ cell culture. mpkCCD$_{cl4}$ cells were developed as a line expressing the characteristics of the principal cell type of the distal nephron and cortical collecting duct. mpkCCD$_{cl4}$ cells were grown in a humidified chamber at 37° C. and 5% $CO_2$. The cell line was maintained in plastic culture flasks for propagation. For electrophysiological measurements, the cells were seeded onto Transwell filters at ¼ confluent density. The media was replaced thrice weekly and consisted of Dulbecco's modified Eagle's medium (DMEM): Ham's F12 basal media supplemented with 2% fetal bovine serum, 1 mM Glutamax, 25 U/mL penicillin, 25 mg/mL streptomycin, 12 mg/L ciprofloxacin, 5 mg/L transferrin, 20 µg/L sodium selenite, and $10^{-7}$ M triiodothyronine.

Example

Electrophysiology. Ussing-style electrophysiological measurements were used to measure net transepithelial transport as well as to monitor the transepithelial resistance as described previously. Briefly, transwell permeable membranes containing confluent (>10 days post seeding) monolayers of mpkCCD$_{cl4}$ cells were excised from the plastic supports, mounted in modified Ussing chambers, and connected to a DVC-1000 Voltage/Current Clamp (World Precision Instruments) with voltage and current electrodes on either side of the membrane. The cells were bathed in serum-free medium maintained at 37° C. via water-jacketed buffer chambers on either side of the filter. Medium was circulated and kept at constant pH using a 5% $CO_2$/95% $O_2$ gas lift. The spontaneous transepithelial potential difference was measured and then clamped to zero. The resulting short-circuit current (SCC) is a measure of net transepithelial ion transport. During the entire experiment, non-zero voltage pulses are induced every 200 seconds and the current displacement during the pulse is used to calculate the transepithelial resistance via Ohm's law. Cultures with resistances lower than 1000 $\Omega \cdot cm^2$ measured within the first 10 minutes of placement in the chambers were discarded. The basal level of transport was monitored for 20-40 minutes before the start of an experiment. The time of addition of the stimulatory effector is defined as zero time.

Unless otherwise stated, each experiment was repeated 3-4 times. Because of variability in the magnitude of the stimulatory responses to cyst fluid from various patients, only one representative experiment is depicted. Unless otherwise stated, all other experiments in the series demonstrated similar responses.

Example

LPA measurements. Levels of LPA molecular species were measured by extraction of cyst fluid followed by quantitation by tandem mass spectrometry on a Agilent 6410 Triple Quadrapole Mass Spectrometer. Cyst fluid (1 ml) with 125 ng 14:0 LPA internal standard was extracted in quadruplicate by vortexing with 4 ml MeOH:CHCl$_3$ (2:1) acidified with 0.2 ml 6 N HCl followed by cooling at −20° C. for 30 min. The phases were then split by the addition of 1 ml CHCl$_3$ and 1.25 ml H$_2$O, vortexing, and centrifugation 13,000×g for 20 min. The lower phase was removed and the upper aqueous phase re-extracted with 2.5 ml CHCl$_3$. The pooled CHCl$_3$ phases were evaporated to dryness under N$_2$ and dissolved in 50 µl MeOH:CHCl$_3$:300 mM ammonium acetate (665:300:35), microfuged at 13,000×g to remove particulate matter, and transferred to HPLC vials. Extracted samples (8 µl) and calibration curve samples (8 µl; 0.1 to 5 ng/µl of each 16:0, 18:0, and 18:1 LPAs with 2.5 ng/µl 14:0 LPA internal standard) were introduced into the electrospray ionization source (negative polarity) by flow injection (MeOH:H$_2$O (1:1) solvent) using Agilent G1367A binary capillary pump (90 µl/min flow rate) and G1377C Micro WPS autosampler with 75 µm internal diameter PeekSil capillary tubing. Instrument settings were source capillary voltage, 4000 V; gas temperature, 300° C.; gas flow, 6 l/min, nebulizer pressure, 15 psi. LPA molecular species (18:0, m/z=437.3; 18:1, m/z=435.3; 16:0, m/z=409.2; 14:0 m/z=381.2) were quantitated by multiple reaction monitoring following two product ions of m/z=153 and 79 with 150 to 164 V fragmentor voltages and 14 to 18 V CE (collision energy) for m/z=153 product ion and 54 to 70 V CE for the m/z=79 product ion; each with 50 msec dwell time. Agilent Mass Hunter Quantitative Analysis software (version B.01.04) was used to process data.

Example

The functional effects of cyst fluid were measured as changes in net transepithelial ion transport across high resistance epithelia formed by the mpkCCD$_{cl4}$ cell line. This line displays the characteristics of the principal cell type of the distal tubules and cortical collecting duct including responses to steroid and peptide hormones. For electrophysiological measurements, confluent cell monolayers grown on permeable supports are mounted in Ussing chambers with access to both the basolateral and apical surfaces. The spontaneous transepithelial potential difference is measured and clamped to zero. In high resistance epithelia, the resulting short-circuit current (SCC) is a measure of net transepithelial transport. By convention, a positive change is defined as anion moving in a secretory direction (serosal to luminal bathing media) or a cation moving in an absorptive direction (luminal to serosal bathing media). Likewise, a decrease in SCC can be defined as anions or cations moving in the opposite direction from that described above. The nature and direction of the ion flux is characterized by effectors and inhibitors.

The majority of the basal current measured before the addition of effectors is due to the flux of Na$^+$ in an absorptive direction. This can be inhibited by the addition of amiloride, a specific inhibitor of the epithelial sodium channel (ENaC), located in the apical membrane. ENaC forms the first step in net sodium movement in a reabsorptive direction in the principal cell type and is one of the main targets of hormones that regulate renal salt and fluid balance.

When fluid isolated from renal cysts of ADPKD patients was added to the basolateral bathing media for a final concentration of 10% cyst fluid, there were immediate as well as more prolonged changes in net ion movement (FIG. 1). 30 minutes after the addition of the cyst fluid, amiloride was added to the apical bathing media and this decreased the remaining ion transport to zero.

Figure 1:
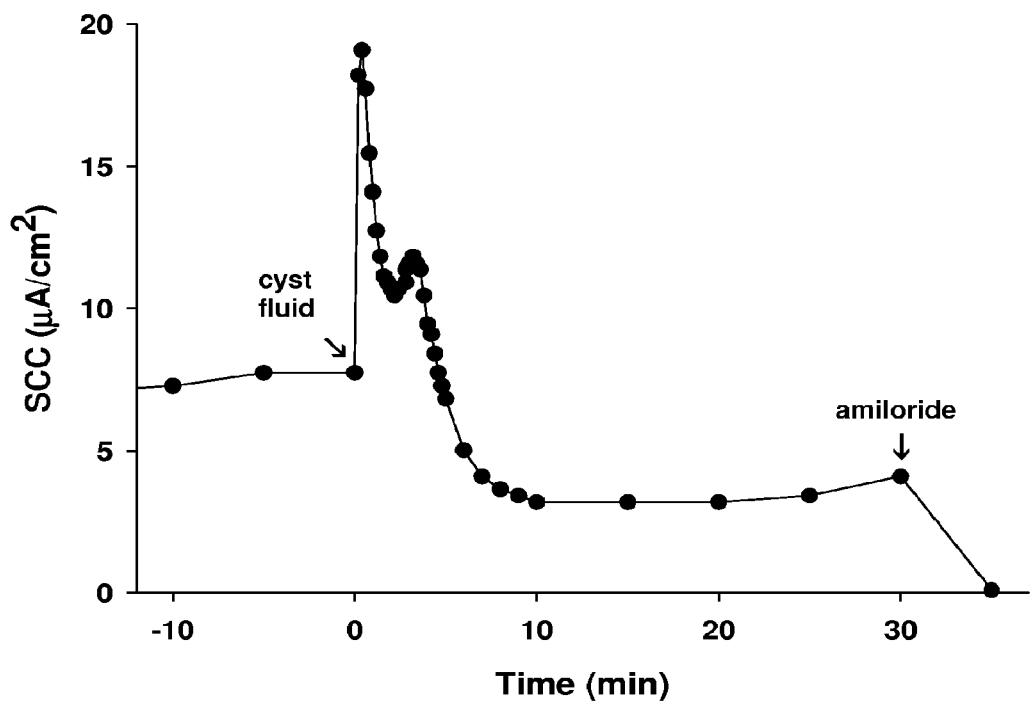
FIG. 1: Cyst fluid stimulation of ion transport in the mpkCCD$_{cl4}$ cell line. mpkCCD$_{cl4}$ cells were grown to confluency on permeable Transwell supports and net ion transport was measured as short circuit current (SCC) using Ussing-chamber electrophysiological techniques. In this experiment the basal SCC was measured for approximately 35 minutes prior to the addition of cyst fluid (time=0) to attain a final concentration of 10% cyst fluid. Only part of this stabilization period is shown on the graph. Amiloride ($10^{-5}$ M) was added to the apical bathing media 30 minutes after the addition of cyst fluid to determine how much of the remaining SCC is due to sodium reabsorption via ENaC. This figure is representative of over 50 experiments performed with cyst fluid from 9 different patients.

In cultures where there was a high basal current (>2 µA/cm$^2$), there were three different types of responses to a single stimulus (FIG. 1). In the first two minutes after addition of the cyst fluid there was an immediate response followed by a less robust peak that was maximal between 4 and 5 minutes after cyst fluid addition. Finally there was a sustained drop below the basal level. This experiment has been repeated using cyst fluids from multiple patients as well as cultures grown months apart. The initial transport peak is consistent in all experiments. The second response that appears maximal at 4-5 minutes after cyst fluid addition is more variable and sometimes is observed as a shoulder of the initial response. The dip below baseline is only seen in those cultures that display a high basal current.

Cyst fluid from 11 different ADPKD patients was tested. 9 of the 11 produced changes in ion transport in the mpkCCD$_{cl4}$ cell line. In all 9 cases, the patterns of the ion transport responses were similar to the pattern illustrated in FIG. 1, albeit with different levels in the magnitude of the response. The remaining two cyst fluids produced no change in ion transport. In the following experiments, cyst fluids from several patients were used because there was insufficient fluid from a single patient to perform all experiments. However, it is important to note that the fluids that provided the most robust responses were used preferentially.

Example

Figure 2:
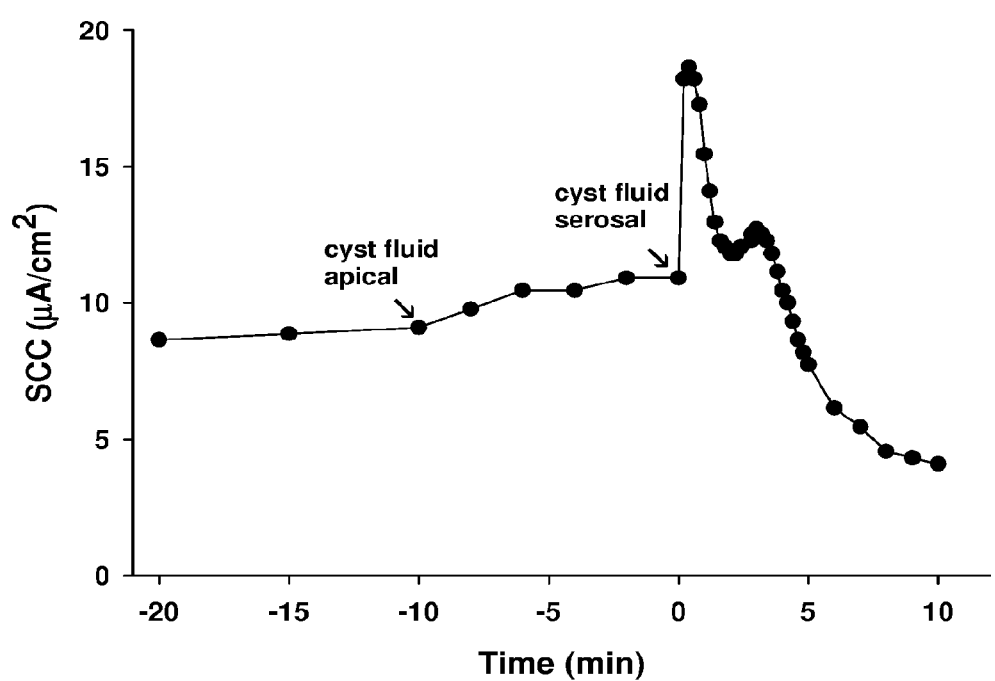
FIG. 2: Sidedness of cyst fluid stimulation of ion transport in the mpkCCD$_{cl4}$ cell line. mpkCCD$_{cl4}$ cells were grown to confluency on permeable Transwell supports and net ion transport was measured as short circuit current (SCC). At time t=−10 minutes, cyst fluid was added to the apical bathing media to obtain a final concentration of 10%. 10 minutes later, cyst fluid was added to the serosal bathing media to obtain a final concentration of 10%. In both cases, an equal volume of fluid was added to the contralateral side to balance the addition of the cyst fluid.

High resistance epithelia are polarized with different proteins and lipids composing the apical and basolateral membranes. To determine if the active component of the cyst fluid required a receptor or other membrane-specific component, the cyst fluid was added first to the apical bathing media and after 10 minutes to the serosal media (FIG. 2). Apical addition failed to elicit the characteristic ion transport response. However basolateral addition to the same culture caused the typical response seen in FIG. 1. Cyst fluid from the same patient was used for the experiments shown in FIGS. 1 and 2. These results indicate that the initial step in the stimulatory response is based in the basolateral membrane and likely is not dependent on a factor that can easily diffuse through the cell membrane to stimulate an intracellular effector.

The overall changes in ion transport mpkCCD$_{cl4}$ cells in response to cyst fluid are not typical of those elicited in response to any hormonal stimulation. Pretreatment with specific inhibitors can be used to determine the contribution of various transport processes and the specific channels involved.

Example

Figure 3:
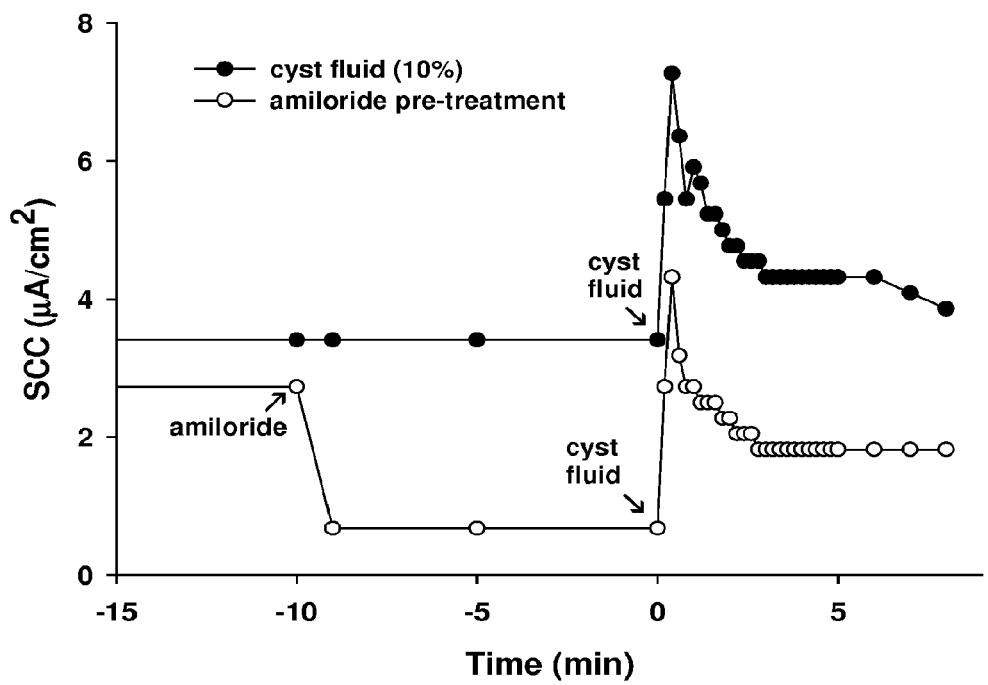
FIG. 3: Effect of amiloride pretreatment on cyst fluid stimulation of ion transport in the mpkCCD$_{cl4}$ cell line. mpkCCD$_{cl4}$ cells were grown to confluency on permeable Transwell supports and net ion transport was measured as short circuit current (SCC). Amiloride ($10^{-5}$ M) was added to the apical bathing media of one of two culture grown and analyzed in parallel. 10 minutes after addition of amiloride, renal cyst fluid from the same patient (10% final volume) was added to the serosal bathing media of both cultures.

Since the majority of the basal SCC is due to ENaC-mediated Na$^+$ flux, amiloride addition to a stabilized monolayer causes an immediate decrease in the basal current (FIG. 3). Addition of cyst fluid from the same patient to control and amiloride pre-treated cells resulted in a similar pattern of changes in ion flux (FIG. 3). These results indicate that ENaC-mediated Na$^+$ transport is not involved in the response to cyst fluid stimulation.

Example

Pre-treatment with a variety of Cl$^-$ channel blockers with varying degrees of specificity (e.g., NPPB (5-Nitro-2-(3-phenylpropyl amino)-benzoic acid, niflumic acid, glibenclamide, and CFTRinh-172) indicated that the major ion transport response to cyst fluid may be a combination of Cl$^-$ secretory events via the cystic fibrosis transmembrane regulator (CFTR) and the recently described TMEM16a. This was confirmed using two specific inhibitors. GlyH-101 is a specific inhibitor of CFTR while tannic acid has recently been shown to specifically inhibit TEM16a, a Ca$^{2+}$-activated Cl$^-$ channel. FIG. 4 illustrates the effects of pretreatment with GlyH-101, tannic acid and a combination of the two Cl$^-$ channel inhibitors on cyst fluid stimulated ion transport.

Neither inhibitor alone completely blocked the response while the two in combination almost completely inhibited the stimulated ion transport response. As depicted in FIG. 4, GlyH-101 causes a stimulatory response when added but this returns to baseline before the addition of the cyst fluid.

Without being bound by theory, it is believed herein that other transporters are also either directly or secondarily involved in the stimulatory response. For example, increases in intracellular Ca$^{2+}$ will also activate Ca$^{2+}$ gated K channels. In this regard, pretreatment with Ba$^{2+}$ on the serosal side inhibited stimulated Cl$^-$ secretion by about 50% while pretreatment on the apical face was without effect. The identity and role of the alternate channels involved in the response are beyond the scope of this work which is predominately directed to identifying the active components in the cyst fluid.

Example

Previous studies conducted in the MDCK cell line and in primary cultures of PKD renal epithelia have indicated that the stimulatory activity in human cyst fluid is a lipid-like molecule that has been identified as an endogenous mammalian forskolin. However within the context of a different renal cell model and a different assay technique, forskolin stimulated response similar to that obtained with cyst fluid was not observed (FIG. 5).

Forskolin caused a slow, sustained increase in transport to a maximal level that was completed inhibited by amiloride. Likewise, pre-treatment with amiloride completely eliminated a subsequent response to forskolin. These results indicate that the forskolin-stimulated ion transport is predominately due to transepithelial Na$^+$ transport mediated via ENaC. However, this cation-specific channel does not appear to play a role in cyst fluid stimulated transport in the current studies (FIG. 3).

Example

Proteomic analysis of cyst fluid has indicated that it is surprisingly rich in a diverse array of proteins. To determine whether the active component of the fluid is a protein, a sample of cyst fluid was boiled for 10 minutes to denature the fluid protein component. The boiled cyst fluid caused the same response in the renal cells as the non-denatured fluid (FIG. 6 as compared to FIGS. 1-4). These results indicate that the active component is not a protein.

Several bioactive lipids have been shown to stimulate or inhibit ion transport in high resistance epithelia. The majority of these are prostaglandins formed by the action of cyclooxygenase. A 30 minute pre-incubation with indomethacin, a nonselective inhibitor of cyclooxygenase was used to determine the role, if any, of prostaglandin synthesis catalyzed by the addition of cyst fluid to the basolateral membrane. Indomethacin pre-treatment did not alter the cyst fluid stimulation of ion transport in the mpkCCD$_{cl4}$ cell line (FIG. 7a).

Two other bioactive lipid mediators are lysophosphatic acid (LPA) and sphingosine-1-phosphate (S-1-P). High concentrations of both of these lipids stimulated ion transport in the mpkCCD$_{cl4}$ cell line. However, the S-1-P responses were consistently minimal compared to those elicited by LPA (FIG. 7B). In addition, the ion transport response to LPA was identical to the response to renal cyst fluid.

A limited dose response for LPA indicated that concentrations from 0.5 to 50 µM LPA stimulated a maximal response in the mpkCCD$_{cl4}$ cell line. In FIG. 7C, responses to concentrations from 0.01 to 1 µM LPA are compared to 10% cyst fluid. 5 and 50 µM were also used in this series and the responses to these high concentrations were not different than the cyst fluid.

Example

Multiple reaction monitoring by tandem mass spectrometry was used to quantitate the concentration of LPA molecular species in the cyst fluid collected from one patient. The cyst fluid contained 3.95+0.40 µM 16:0 LPA, 1.42+0.043 µM 18:1 LPA and 18:0 LPA present at levels too low to quantitate with our methods. The combined concentrations of the various species are above 5 µM and, therefore, based on the dose response relationship, addition of cyst fluid at a 10% volume/volume dilution (final LPA concentration above 0.5 µM) would stimulate a maximal response.

LPA responses are mediated via a family of receptors. In polarized epithelial cells, these receptors are found predominately on the basolateral membrane. To determine the nature of the LPA receptors and to provide a further indication of the nature of the active component of the cyst fluid, the renal cells were treated with several LPA receptor antagonists/agonists.

L-NASPA (N-palmitoyl-L-serine phosphoric acid) has been described as an LPA receptor antagonist with some agonist properties. Other studies have found NASPA to be an LPA mimetic. Interestingly, in the current studies there are indications of all of these effects (FIG. 8A). When NASPA is added to the basolateral bathing media, there is an immediate response that mimics the response to LPA or 10% cyst fluid. The L-NASPA pre-treatment appears to inhibit a subsequent response to cyst fluid. Identical effects have been observed in 4 separate experiments.

DGPP (diacylglycerol pyrophosphate) is a LPA1/LPA3 receptor antagonist. Pretreatment with 20 µM DGPP substantially inhibited the Cl⁻ secretory transport stimulated in response to 10% cyst fluid (FIG. 8B). In five such experiments, the average inhibition of the Cl⁻ secretory peak was 72.8+4.49%. These studies suggest that a substantial portion of the cyst fluid effect is mediated by with the LPA1 or LPA3 receptor. Higher concentrations of DGPP may have fully inhibited the cyst fluid response but concentrations of the antagonist above 20 µM had an adverse effect on the integrity of the cellular monolayer as evidenced by a decrease in transepithelial resistance. DDP (dodecylphosphate) is a LPA2 agonist/LPA3 antagonist. Pretreatment with DDP had no effect on the stimulatory effect of the cyst fluid (FIG. 8C).

When considered together with the previous data, the results presented in FIG. 8 substantiate the contention that the active component of the cyst fluid in LPA. Furthermore, the results suggest that a pertinent LPA receptor mediating the effect is LPA1.

High levels of free LPA in cyst fluid would be expected to diffuse across the epithelial barrier and interact with receptors on the basolateral membrane. However, under normal conditions there is no evidence of such on-going stimulation. One possible explanation is that the LPA is bound to proteins that are abundant in the cyst fluid and, therefore, retained inside the cyst where it is protected from receptor interaction. Size fractionation of the active component of cyst fluid confirms this supposition. Untreated cyst fluid was separated into fractions above and below 100 kDa using Centri-prep centrifuge filters. As shown in FIG. 9, the filtrate containing components less than 100 kDa had very little stimulatory activity while the fraction with components approximately 100 kDa and higher showed a stimulatory activity that was virtually identical to the unfractionated cyst fluid. For comparison, the cyst fluid used in this experiment is the same as that shown in FIG. 1.

LPA is also present in serum, particularly during inflammatory responses. Therefore we tested the ability of fetal bovine serum (FBS) to stimulate a similar secretory response in mpkCCD$_{cl4}$ epithelial cells. The addition of a 10% concentration of FBS elicited a response in the renal cells that was virtually identical to the response caused by the cyst fluid (FIG. 10).

What is claimed is:

1. A method for reducing electrolyte and fluid secretion in a patient having or suspected of having a cystic disease, the method comprising the step of administering to the patient (a) an effective amount of one or more TMEM16a inhibitors; and (b) an effective amount of one or more lysophosphatidic acid antagonists, or an effective amount of one or more PPAR gamma agonists, or a combination thereof.

2. The method of claim 1 wherein the one or more lysophosphatidic acid antagonists are selected from the group consisting of DGPP, cyclic sulfuric acid analogs of 2-oleoyl LPA, Ki16425, L-NASPA, VPC 12204, VPC 12249, VPC 12249-10t, VPC 12249-10t-13d, VPC 32179, VPC 32183, VPC 12031, Thio-ccPA-18:1, Thio-ccPA-16:0, CHF-ccPA, Palmitoyl α-bromomethylene phosphonate, Palmitoyl α-chloromethylene phosphonate, Palmitoyl α-H2-methylene phosphonate, Palmitoyl α-OH-methylene phosphonate, Oleoyl sn-2-AO-LPA, Palmitoyl sn-2-AO-LPA, Alkoxymethylene-phosphonate-LPA (18:1), Alkoxymethylene-phosphonate-LPA (16:0), FAP-10, FAP-12, SPH, SPP, N-palmitoyl-l-serine, N-palmitoyl-l-tyrosine, 2-Amino-3-oxo-3-(tetradeeylamino) propyl dihydrogen phosphate, 2-(Acetylamino)-3-oxo-3-(tetradecylamino) propyl dihydrogen phosphate, 2-Amino-3-(octadecylamino)-3-oxopropyl dihydrogen phosphate, 1,2-(3-Octadecyloxypropane)-bis (dihydrogen phosphate), 1,2-(3-Docosanoyloxypropane)-bis (dihydrogen phosphate), Phosphoric acid monobutyl ester, Phosphoric acid monooctyl ester, Phosphoric acid monooctadecyl ester, Phosphoric acid monodocosyl ester, Acyl LPG 18:1, DPIEL, LPG 14:0, 2(s)-OMPT, 3-(N-((2-(2-((pyridin-3-ylmethylamino) carbonyl)phenyl)phenyl)carbonyl)-N-(2-(2,5-dimethoxyphenyl-) ethyl)amino) propanoic acid hydrochloride, methyl 3-(14-[4-(1[1-(2-chlorophenyl)ethoxy]carbonyl}amino)-3-methyl-5-isoxazolyl]benzyl}sulfanyl)propanoate, and 4'-1[(3-phenylpropyl) (3,4,5-imethoxybenzoyl)amino]methyl}-2-biphenylyl)acetic acid, and pharmaceutically acceptable salts of the foregoing.

3. The method of claim 1 wherein one of the lysophosphatidic acid antagonists is VPC 32183, or a pharmaceutically acceptable salt thereof.

4. The method of claim 1 wherein at least one of the lysophosphatidic acid antagonists reduces the activity of lysophosphatidic acid at one or more lysophosphatidic acid receptors selected from the group consisting of LPA1, LPA2, LPA3, LPA4, and LPA5.

5. The method of claim 1 wherein one of the TMEM16a inhibitors is tannic acid or a pharmaceutically acceptable salt thereof, or a prodrug of any of the foregoing.

6. The method of claim 1 wherein the cystic disease is selected from the group consisting of polycystic kidney disease, Bardt Biedl syndrome, nephronophthisis, Meckel Gruber syndrome, and oral-facial-digital syndrome.

7. The method of claim 1 wherein the patient in need thereof has a cyst residing in an internal organ selected from the group consisting of kidney, liver, and pancreas.

8. The method of claim 1 wherein the lysophosphatidic acid antagonist is administered orally, parenterally, or by injection.

9. The method of claim 8 wherein the lysophosphatidic acid antagonist is administered by a method selected from the group consisting of intravenous injection, intrahepatic injection, intrarenal injection, intrapancreatic injection, direct infusion, and combinations thereof.

10. The method of claim 1 wherein the lysophosphatidic acid antagonist is administered via an implanted device.

11. The method of claim 1 wherein one of the lysophosphatidic acid antagonists is VPC 51299.

* * * * *